US010806734B2

(12) United States Patent
Christ et al.

(10) Patent No.: US 10,806,734 B2
(45) Date of Patent: Oct. 20, 2020

(54) FUNCTIONAL CURE OF RETROVIRAL INFECTION

(71) Applicant: KATHOLIEKE UNIVERSITEIT LEUVEN, Leuven (BE)

(72) Inventors: Frauke Christ, Heverlee (BE); Zeger Debyser, Heverlee (BE); Rik Gijsbers, Blanden (BE); Lenard Vranckx, Hulshout (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 15/559,077

(22) PCT Filed: May 9, 2016

(86) PCT No.: PCT/EP2016/060314
§ 371 (c)(1),
(2) Date: Sep. 18, 2017

(87) PCT Pub. No.: WO2016/180770
PCT Pub. Date: Nov. 17, 2016

(65) Prior Publication Data
US 2018/0071288 A1 Mar. 15, 2018

(30) Foreign Application Priority Data

May 8, 2015 (GB) .................................. 1507859.5
May 8, 2015 (GB) .................................. 1507866.0

(51) Int. Cl.
C12Q 1/70 (2006.01)
C12P 19/34 (2006.01)
A61K 31/505 (2006.01)
A61K 45/06 (2006.01)
A61K 31/44 (2006.01)
A61K 31/00 (2006.01)
A61K 48/00 (2006.01)

(52) U.S. Cl.
CPC ............ *A61K 31/505* (2013.01); *A61K 31/00* (2013.01); *A61K 31/44* (2013.01); *A61K 45/06* (2013.01); *A61K 48/005* (2013.01); *C12N 2740/16043* (2013.01)

(58) Field of Classification Search
None
See application file for complete search history.

(56) References Cited

U.S. PATENT DOCUMENTS 6,207,455 B1 * 3/2001 Chang ................ A01K 67/0271
435/320.1
2012/0136023 A1 5/2012 Bell et al.
2013/0245049 A1 9/2013 Chaltin et al.
2014/0315927 A1 10/2014 Bell et al.
2015/0336965 A1 11/2015 Chaltin et al.

FOREIGN PATENT DOCUMENTS

WO 2012065963 A2 5/2012
WO 2012066442 A1 5/2012

OTHER PUBLICATIONS

Christ et al Rational design of small-molecule inhibitors of the LEDGF/p75-integrase interaction and HIV replication Nature Chemical Biology 2010; pp. 442-448.*
Vranckx et al LEDGIN-mediated Inhibition of Integrase—LEDGF/p75 Interaction Reduces Reactivation of Residual Latent HIVEBioMedicine, vol. 8, Jun. 2016, pp. 14-15.*
Mesplède et al., Will LEDGIN molecules be able to play a role in a cure for HIV infection? EBioMedicine 8 (2016) 14-15.*
Marini et al Nuclear architecture dictates HIV-1 integration site selection May 14, 2015 | vol. 5 2 1 | N AT U R E | 2 2 7-231.*
Laird et al Rapid Quantification of the Latent Reservoir for HIV-1 Using a Viral Outgrowth Assay PLOS Pathogens May 2013 | vol. 9 | Issue 5 | e1003398-e1003398.*
Demeulemeester et al., LEDGINs, non-catalytic site inhibitors of HIV-1 integrase: a patent review (2006-2014) Expert Opin. Ther. Patents (2014) 24(6):609-632.*
Dahl et al., Review HIV reservoirs, latency, and reactivation: Prospects for eradication Antiviral Research 85 (2010) 286-294.*
Jurado et al 2013 Multimodal Mechanism of Action of Allosteric HIV-1 Integrase Inhibitors. Expert Reviews in Molecular Medicine pp. 1-22.*
PCT International Search Report and Written Opinion dated Jul. 15, 2016 for PCT International Patent Application No. PCT/EP2016/060314, 18 pages.
Gijsbers R et al: LEDGF Hybrids Efficiently Retarget Lentiviral Integration Into Heterochromatin, Molecular Therapy, vol. 18, No. 3, Mar. 2010, pp. 552-560.
Vallejo A et al: The effect of intensification with raltegravir on the HIV-1 reservoir of latently infected memory CD4 T cells in suppressed patients, AIDS. vol. 26, No. 15, Sep. 2012, pp. 1885-1894.
Katlama C et al: Barriers to a cure for HIV: new ways to target and eradicate HIV-1 reservoirs, The Lancet, vol. 381, No. 9883, Jun. 2013, pp. 2109-2117.

(Continued)

*Primary Examiner* — Maria G Leavitt
(74) *Attorney, Agent, or Firm* — Amster, Rothstein & Ebenstein LLP

(57) ABSTRACT

The application relates to methods of curing retroviral infections, i.e. ensuring remission of retroviral infections, more particularly HIV infections, by administering a compound which is capable of binding to the LEDGF/p75 binding pocket of HIV-integrase and inhibiting LEDGF/p75-IN protein-protein interaction. The application further relates to the use of LEDGINs in retroviral gene therapy.

9 Claims, 21 Drawing Sheets
Specification includes a Sequence Listing.

(56) References Cited

OTHER PUBLICATIONS

Malet I et al: The future of integrase inhibitors of HIV-1, Current Opinion in Virology, vol. 2, No. 5, Oct. 2012, pp. 580-587.
Meehan A M et al: Chromatin tethering and retroviral integration: Recent discoveries and parallels with DNA viruses, BBA—Gene Regulatory Mechanisms, vol. 1799, No. 3-4, Mar. 2010, pp. 182-191.

\* cited by examiner

A

B

A

A

B

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgcaccctgt gtctcaacat                                           20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggcttcaagg ttgtctctgg                                           20

<210> SEQ ID NO 3
<211> LENGTH: 20
<212> TYPE: DNA
<213> ORGANISM: Artificial Sequence
<220> FEATURE:
<223> OTHER INFORMATION: tCD34 probe
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (20)..(20)
```

-continued

<223> OTHER INFORMATION: TAM

<400> SEQUENCE: 3
ggccacaaca aacatcacag                                                                                      20

FUNCTIONAL CURE OF RETROVIRAL INFECTION

CROSS-REFERENCE TO RELATED APPLICATIONS

This application is a U.S. national stage entry under 35 U.S.C. § 371 of PCT International Patent Application No. PCT/EP2016/060314, filed May 9, 2016, which claims priority to Great Britain Patent Application No. 1507866.0, filed May 8, 2015 and Great Britain Patent Application No. 1507859.5, filed May 8, 2015, the contents of which are incorporated herein by reference in their entirety.

FIELD OF THE INVENTION

The application relates to methods of curing retroviral infections, more particularly HIV infections. The application further provides compositions suitable for use in these methods. The application further relates to the use of LEDGINs in retroviral gene therapy.

BACKGROUND

The development of antivirals in the last two decades revolutionized the treatment of HIV/AIDS turning the disease into a chronic illness rather than a life-threatening disorder.

Typically, treatment of HIV/AIDS involves the use of multiple antiretroviral drugs in an attempt to control HIV infection. Antiretrovirals inhibit HIV replication by interference with one of the viral replication steps. Different classes of antiretroviral agents have been developed. Entry inhibitors interfere with binding, fusion and entry of HIV-1 into the cell. Nucleoside or non-nucleoside reverse transcriptase inhibitors (NRTI or NNRTI) and nucleotide reverse transcriptase inhibitors (NtRTI) inhibit reverse transcription of HIV RNA. Integrase inhibitors (also known as integrase nuclear strand transfer inhibitors or INSTIs) inhibit the viral enzyme integrase. Protease inhibitors (PI) block the viral protease enzyme necessary to produce mature virions upon budding from the host membrane. These five different classes are combined in different ways referred to as antiretroviral therapy (ART), combination anti-retroviral therapy (cART) or highly active anti-retroviral therapy (HAART).

Antiretroviral molecules that prevent the binding of retroviral integrase (IN) to LEDGF/p75 thereby interfering with the catalytic activity of IN have been developed (Christ et al., 2010). These molecules belong to different chemical classes but all bind to the LEDGF/p75 binding pocket of HIV-1 integrase (Christ and Debyser, 2013; Debyser et al., 2015). These compounds have been referred to as "LEDGINs", an acronym based on their ability to bind the LEDGF/p75 binding pocket in IN.

LEDGINs have also been found to also affect late stage HIV replication and it has been suggested that their potency is mainly determined by their effect on HIV particle maturation (Jurado et al., 2013). Based thereon, their therapeutic value would primarily be in combination with other antiretroviral drugs to suppress HIV replication in a chronic therapy.

Current antiretroviral therapies cannot cure the infection due to the existence of a reservoir of latently infected cells. While HIV actively replicates in activated CD4+ T lymphocytes, it is able to reside in a long-lived quiescent state in memory resting CD4+ T cells. This latently infected cell population is established early during the course of infection and encompasses only a small fraction of the total CD4+ T cells in patients (about 1 in $10^6$ cells). This enables HIV persistence during antiretroviral therapy and is responsible for the rebound of viremia upon therapy cessation. As a result antiretroviral therapy of HIV infection is in principle a chronic and suppressive therapy.

Accordingly remains a need for curative treatments of retroviral infections.

SUMMARY OF THE INVENTION

The present inventors have found that compounds capable of interfering with the binding of retroviral IN to LEDGF/p75 thereby inhibiting IN enzymatic activity (defined as LEDGINs) are in fact capable of reducing the number of integrated proviruses and ensure retargeting of integration thereby inducing a transcriptionally silent state of the residual retroviral reservoir that is resistant to reactivation. Accordingly, treatment of patients with active viremia with an appropriate dosage of LEDGINs will not only suppress retroviral replication as other anti-retrovirals do, but will moreover ensure that the viral reservoir established cannot be reactivated, thereby effectively providing a functional cure or remission of the retroviral infection.

Accordingly, the application provides methods for curing a retroviral infection in an animal which comprise administering a compound that binds to the LEDGF/p75 binding pocket of HIV-integrase thereby inhibiting LEDGF/p75-IN protein-protein interaction to said animal and provides compounds for use in such methods. In these methods, efficacy of the cure can be determined by determining the reactivation potential of the retroviral reservoir.

The application thus provides a compound which is capable of binding to the LEDGF/p75 binding pocket of HIV-integrase and inhibiting LEDGF/p75-IN protein-protein interaction for use in a method of curing a retroviral infection in an animal, which method comprises administering said compound to said animal and determining the efficacy of said cure by determining the reactivation potential of the retroviral reservoir of said animal, so as to determine whether or not treatment can be interrupted or stopped. More particularly, the method comprises determining the reactivation potential of the retroviral reservoir of said animal and either stopping the administration or starting a new dosage regimen of said compound based on the outcome of said determination.

As a functional cure or remission is envisaged, the method does not require life-long treatment. More particularly, administration is envisaged only during a discrete period of time. In particular embodiments, the duration of administration is determined based on the efficacy of said cure, which is determined by the reactivation potential of the retroviral reservoir of said animal.

In particular embodiments, the duration of administration is determined based on the reactivation potential of the retroviral reservoir. In particular, administration of the compound will be transient until a diagnostic test reveals that the residual reservoir is resistant to reactivation. In particular embodiments, the compound is administered daily during a discrete period of 1 to 52 weeks, such as 1 to 24 weeks.

In particular embodiments the dosage of the compound envisaged for use in the methods provided herein is similar to the dosage envisaged for use in standard therapy. In particular embodiments, the methods involve administering the compound in an acute dosage regimen. In particular embodiments the dosage of the compound is higher, such as at least twice as high as the dosage envisaged for use in standard therapy. In further particular embodiments said dosage is a dosage which ensures a trough concentration in the blood which is at least 5 times, more particularly at least 10 times the antiviral EC50 of said compound.

In particular embodiments, the animal is a treatment-naïve animal. In alternative embodiments, the animal has received standard anti-retroviral combination therapy and said antiretroviral combination therapy is interrupted prior to the administration of said compound. In particular embodiments, the LEDGIN is included in initial cART, and cART is interrupted or stopped.

In the methods envisaged herein treatment with a compound which is capable of binding to the LEDGF/p75 binding pocket of HIV-integrase and inhibiting LEDGF/p75-IN protein-protein interaction is stopped after some time depending on the outcome of a test performed on a sample of said animal determining the reactivation potential of the retroviral reservoir in said animal. In particular embodiments, the treatment is interrupted. This implies that the animal is tested on a regular basis for signs of reactivation of the proviral load (or new infection) and that treatment is reinitiated after a determination that the animal is tested positive for the virus.

As indicated above, it is typically envisaged that the concentration of the compound in the animal should be sufficiently high to ensure an effective cure. In particular embodiments, the compound is administered twice or more a day.

In particular embodiments of the methods provided herein, it is envisaged that the compound is administered as a monotherapy. However, in alternative embodiments, the combination with proteinase inhibitors can also be envisaged.

In particular embodiments, the compound for use as envisaged herein is a compound which inhibits binding to the LEDGF/p75 binding pocket of HIV-integrase thereby inhibiting LEDGF/p75-IN protein-protein interaction; in particular embodiments, the compound is a pyrimidine or pyridine derivative.

A second aspect of the present invention relates to the use of LEDGINs in retroviral gene therapy. The present inventors have found that compounds capable of interfering with the binding of retroviral IN to LEDGF/p75 (also referred to herein as LEDGINs) retarget integration of retroviruses towards safe sites. Accordingly, LEDGINs can be used to improve the safety of retroviral gene therapy.

Accordingly, the present invention provides for the use of a compound capable of interfering with the binding of retroviral IN to LEDGF/p75 in combination with a retroviral vector for introducing a genetic modification into a cell in vitro. In particular embodiments the compound is used in a method for delivering a transgene into a host cell comprising contacting said host cell ex vivo with a retroviral vector comprising said transgene and said compound capable of interfering with the binding of retroviral IN to LEDGF/p75. More particularly the retroviral vector is a lentiviral vector.

Other embodiments, objects, features and advantages will be set forth in the detailed description of the embodiments that follows. The Summary above is to be considered as a brief and general overview of some of the embodiments disclosed herein, is provided solely for the benefit and convenience of the reader, and is not intended to limit in any manner the scope encompassed by the appended claims.

Numbered statements of this invention are:
1. A compound which is capable of binding to the LEDGF/p75 binding pocket of HIV-integrase and inhibiting LEDGF/p75-IN protein-protein interaction for use in a method of curing a retroviral infection in an animal, which method comprises administering said compound to said animal and determining the efficacy of said cure, by determining the reactivation potential of the retroviral reservoir of said animal, so as to determine whether or not treatment can be interrupted.
2. The compound for use according to statement 1, wherein the duration of administration of said compound is determined based on the efficacy of said cure.
3. The compound for use according to statement 1 or 2, wherein the reactivation potential of the retroviral reservoir is determined by measuring the proviral load in said animal.
4. The compound for use according to any one of statements 1 to 3, wherein said compound is administered until the retroviral reservoir is resistant to reactivation.
5. The compound for use according to any one of statements 1 to 4, wherein the daily dosage of said compound is equal to or higher than the dosage envisaged for use in standard therapy.
6. The compound for use according to any one of statements 1 to 5, wherein the daily dosage of said compound is a dosage which ensures a trough concentration in the blood which is at least times 5 times the antiviral EC50 of said compound.
7. The compound for use according to any one of any one of statements 1 to 6, wherein said animal has received standard anti-retroviral combination therapy and said antiretroviral combination therapy is interrupted prior to the administration of said compound.
8. The compound for use according to any one of statements 1 to 6, wherein said animal is a treatment-naïve animal.
9. The compound for use according to any one of statements 1 to 8, wherein said compound is administered as part of an anti-retroviral combination therapy.
10. The compound for use according to any one of statements 1 to 9, wherein said compound is administered daily during a discrete period of 1 to 24 weeks, and the efficacy of said cure is determined after said discrete period of 1 to 24 weeks.
11. The compound for use according to any one of statements 1 to 10, wherein said method comprises administering said drug as a monotherapy.
12. The compound for use according to any one of statements 1 to 11, wherein said compound is a pyrimidine or pyridine derivative.
13. The use of a compound capable of interfering with the binding of lentiviral IN to LEDGF/p75 in combination with a lentiviral vector for introducing a genetic modification into a cell in vitro.
14. A method for delivering a transgene into a host cell comprising contacting said host cell ex vivo with a lentiviral vector comprising said transgene and a compound capable of interfering with the binding of lentiviral IN to LEDGF/p75.
15. A lentiviral vector for use in a method of gene therapy, characterized in that the lentiviral vector is co-administered with a compound capable of interfering with the binding of lentiviral IN to LEDGF/p75.

DETAILED DESCRIPTION

Figure 1:
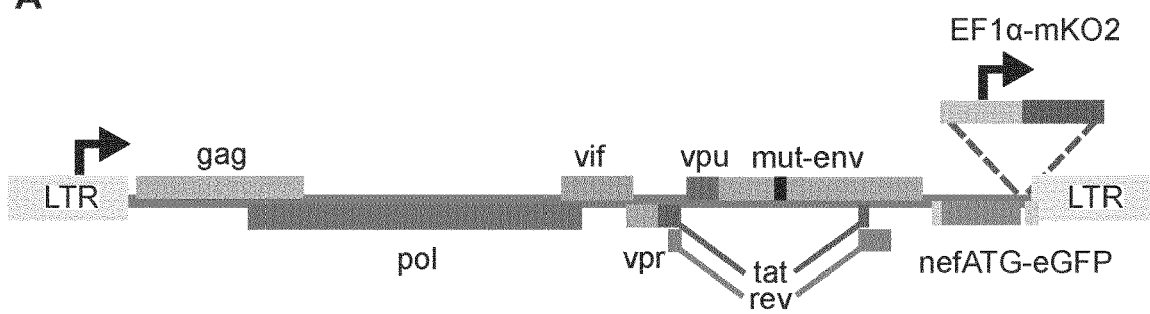
FIG. 1: (A) Schematic representation of the two-colored reporter virus carrying an eGFP driven by the viral LTR promoter in the nef position an entire constitutive transcriptional unit (EF1a-mKO2) inserted downstream. (B) Dot plots representing facs analysis of SupT1 cells infected with the single reporter viral controls (OGH-Delta mKO2, OGH-DeltaeGFP) or the double reporter virus OGH. (C) LEDGF KD affects the fraction of silently infected cells (% eGFP−, mKO2+ cells)/(% mKO2+ cells)*100. Data represent averages of triplicates and error bars indicate the standard deviation. All viruses are VSV-G pseudotyped. GFP, Enhanced Green Fluorescent Protein; mKO2, Mutant Kusubira Orange 2.
Figure 1:
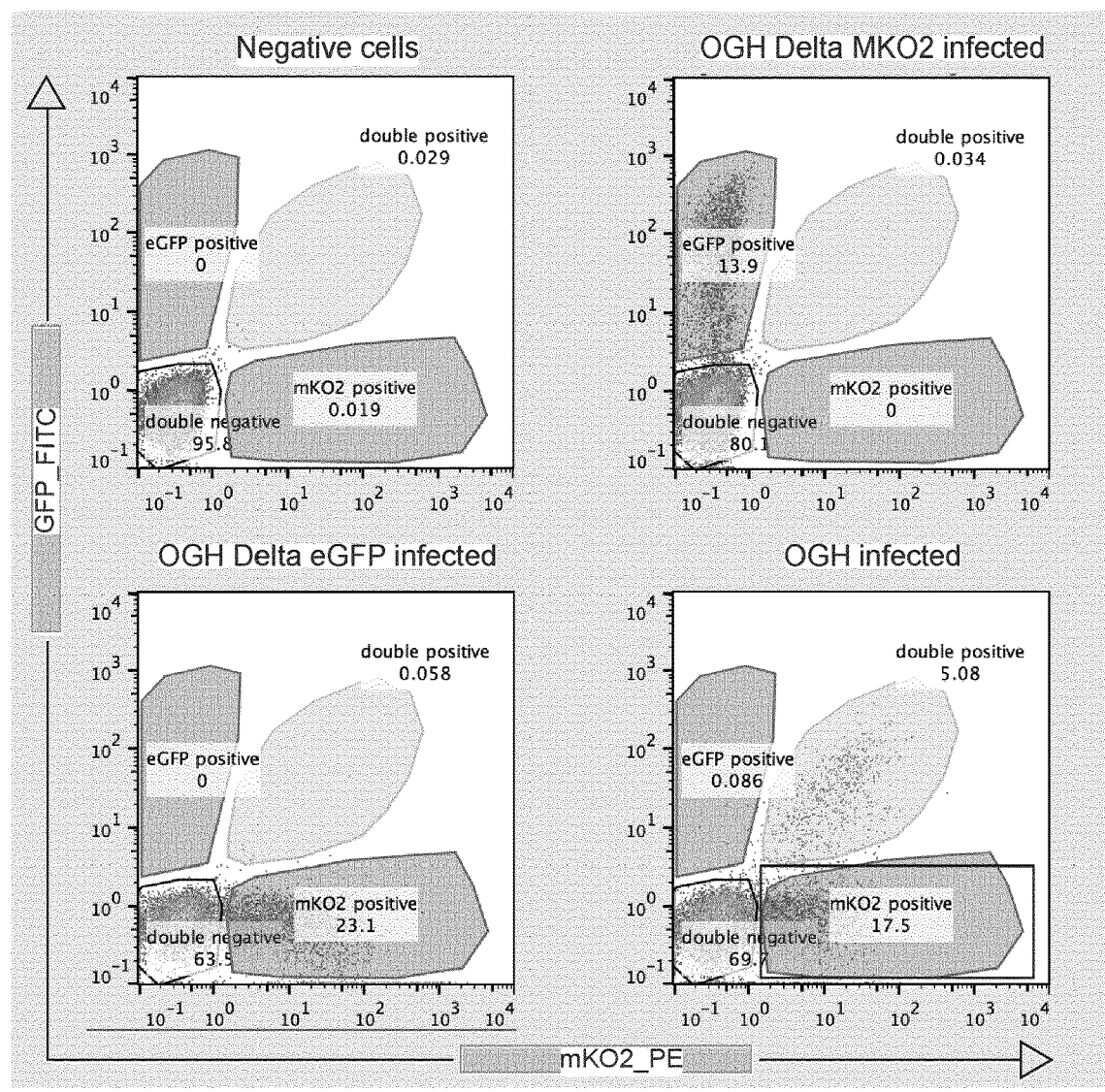
Figure 1:
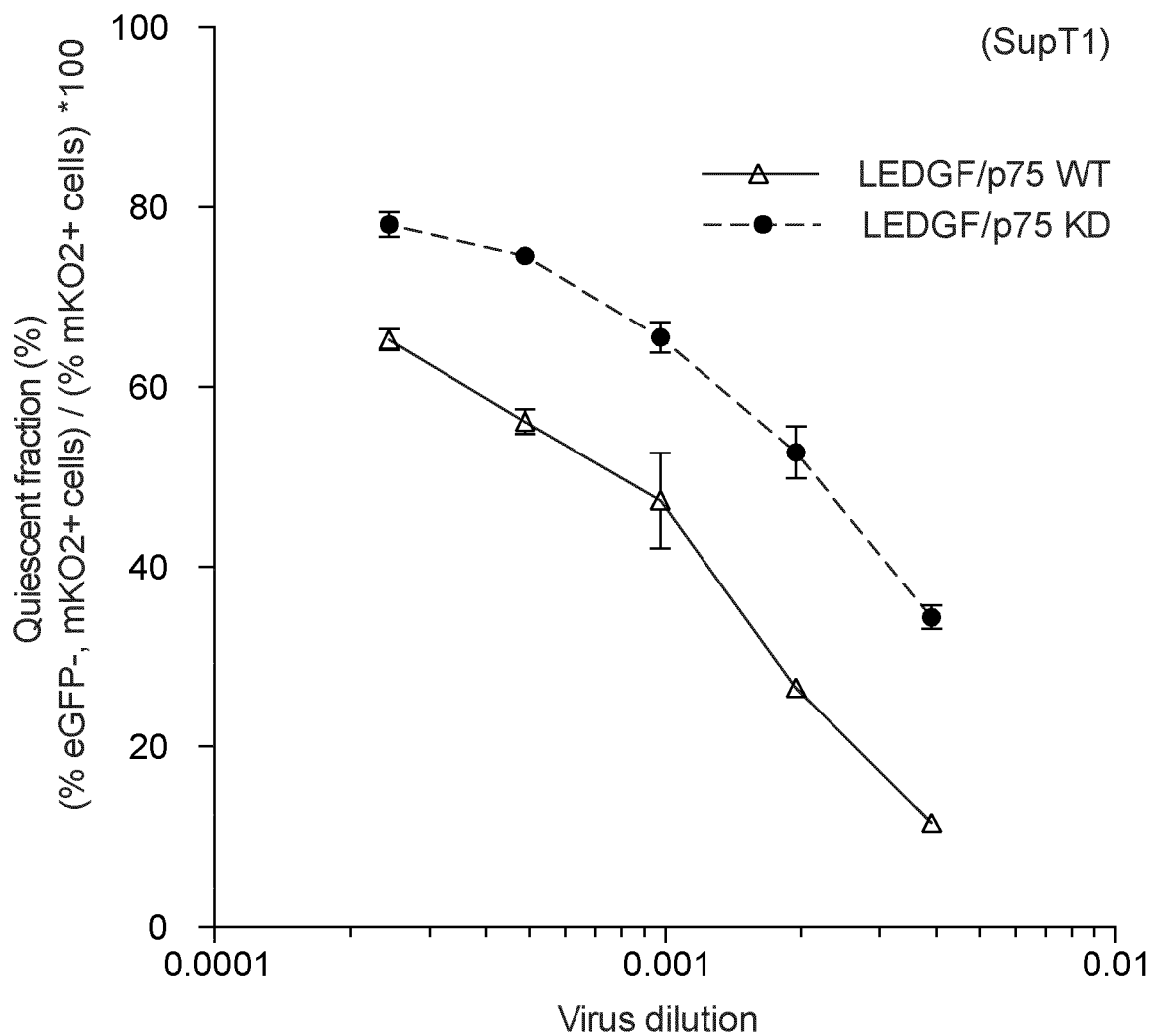

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The term "compound", as used herein, unless otherwise indicated, refers to any specific chemical compound disclosed herein. The term generally refers to a single compound but in some instances the term may also refer to stereoisomers and/or optical isomers (including racemic mixtures) or enantiomerically enriched mixtures of disclosed compounds. As will be detailed herein, the compounds envisaged in the context of the present invention are also referred to as LEDGINs.

The term "patient" or "subject" is used throughout the specification within context to describe an animal, especially including a domesticated mammal and preferably a human, to whom a treatment or procedure is performed. For treatment of those infections, conditions or disease states which are specific for a specific animal such as a human patient, the term patient refers to that specific animal. In most instances, the patient or subject of the present invention is a domesticated/agricultural animal or human patient of either gender.

The term "retrovirus" shall be used to describe a virus from the family of the Retroviridae and its infections, which term shall be used to embrace human and animal retroviruses. The term "human immunodeficiency virus" shall be used to describe human immunodeficiency virus (HIV) and its infections, which term shall be used to embrace both human immunodeficiency virus 1 (HIV-1) and including wild-type (WT) and mutants of HIV.

The term "standard therapy" as used herein refers to the therapy currently envisaged for the management of HIV/AIDS, which involves the combined use of multiple anti-retroviral drugs. Typically the different antiretroviral drugs that are combined act on different stages of the HIV life cycle such as but not limited to nucleoside reverse transcriptase inhibitors (NRTI), non-nucleoside reverse transcriptase inhibitors, protease inhibitors and fusion inhibitors. The therapeutic use of a combination of anti-retroviral drugs is referred to in the art as anti-retroviral therapy (ART), combination anti-retroviral therapy (cART) and as "highly active antiretroviral therapy" (or HAART). Standard therapy involves continuous administration which is life-long.

The term "standard dosage" as used herein to refer to the dosage of an anti-retroviral compound, refers to the dosage envisaged for use in standard therapy. Typically, the dosage envisaged for use in standard therapy is based at least in part on the EC50 of the compound, whereby the aim is to ensure a trough level of the compound in the blood of the patient which is above the EC50 of the compound. Preferably the dosage is determined such that the trough level of the drug in the patient is at least two times, more particularly at least 3 times or more the EC50 value of the compound. Given that standard therapy involves continuous administration the dosage of the compound for standard therapy will in practice take into account both the short term and long term toxicity of the compound.

The term "acute dose" or "acute dosage regimen" as used herein refers to a dosage which is limited in time and which involves the administration of a relatively high amount of the compound. Typically, the dosage is between 2-100 times the dosage of the compound as would be envisaged for use in standard therapy which is a chronic therapy. Examples of acute dosage regimens are provided herein.

The term "effective amount" is used herein to describe an amount of a compound or composition which, in context, is used to ensure a desired result, more particularly in the context of the present invention to ensure retargeting of all DNA of retroviral origin. The term effective subsumes all other effective amount or effective concentration terms which are otherwise described or used in the present application.

The term 'vector' generally refers to nucleic acid molecules, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The term "vector" may thus also be defined as a gene delivery vehicle that facilitates gene transfer into a target cell.

The term "viral vector" as used herein denotes vectors that are derived from viruses including but not limited to: retrovirus, including lentivirus, adeno-associated virus, adenovirus, herpesvirus, hepatitis virus or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. In the context of the present invention a "retroviral vector" is a vector that is retrieved from a retrovirus.

The term "transgene" as used herein refers to particular nucleic acid sequences encoding a polypeptide or a portion of a polypeptide to be expressed in a cell into which the nucleic acid sequence is inserted. However, it is also possible that transgenes are expressed as RNA, typically to lower the amount of a particular polypeptide in a cell into which the nucleic acid sequence is inserted. These RNA molecules include but are not limited to molecules that exert their function through RNA interference (shRNA, RNAi), micro-RNA regulation (miR), catalytic RNA, antisense RNA, RNA aptamers, etc. Of note, expression of the transgene may be restricted to a subset of the cells into which the nucleic acid sequence is inserted. The term transgene is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By mutant form is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell.

The term "promoter" refers to nucleic acid sequences that regulate, either directly or indirectly, the transcription of corresponding nucleic acid coding sequences to which they are operably linked (e.g. a transgene). A promoter may function alone to regulate transcription or may act in concert with one or more other regulatory sequences (e.g. enhancers or silencers). In the context of the present application, a promoter is typically operably linked to a transgene to regulate transcription of the transgene.

The term "operably linked" as used herein refers to the arrangement of various nucleic acid molecule elements relative to each such that the elements are functionally connected and are able to interact with each other. Such elements may include, without limitation, a promoter, an enhancer, a polyadenylation sequence, one or more introns, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in a vector, the regulatory elements will typically be located immediately upstream of the promoter (although this is generally the case, it should definitely not be interpreted as a limitation or exclusion of positions within the vector), but this needs not be the case in vivo.

The term "gene therapy" refers to a treatment encompassing the administration of a transgene to a patient. The transgene product may be a (e.g. therapeutic or immunogenic) protein, or an RNA molecule to block the expression of a specific gene using RNA interference technology, or the transgene may replace a defective gene in the treatment of a genetic disorder or disease.

Unless defined otherwise, all technical and scientific terms used herein have the same meaning as commonly understood by one of ordinary skill in the art in the field of the invention. Any methods and materials similar or equivalent to those described herein can also be used in the practice or the present invention, but the preferred methods and products are described herein.

The application provides methods for curing a retroviral infection, more particularly an HIV infection, in a human or a non-human animal. Indeed as detailed above, it has been shown that the main cause of persistence of retroviral infections is the existence of a reservoir of latently infected cells which allow the virus to rebound upon cessation of therapy. The present inventors have found that compounds capable of interfering with the binding of retroviral IN to LEDGF/p75 (also referred to as LEDGINs) ensure retargeting of integration and that retargeted HIV integrants are resistant to reactivation. Accordingly, appropriate administration of LEDGINs as envisaged herein ensures that the viral reservoir that is established starting from the early stage of infection cannot be reactivated, thereby effectively providing a curative treatment of retroviral infection. As will be detailed herein, the methods envisaged herein can be applied at any stage of infection where active replication and thus integration takes place.

The application thus provides compounds that are capable of interfering with the binding of retroviral IN to LEDGF/p75 for use in curing a patient of a retroviral infection. These compounds compete with wild-type LEDGF/p75 for binding to HIV integrase and thereby suppressing the function of LEDGF/p75.

Compounds capable of interfering with the binding of retroviral IN to LEDGF/p75 thereby inhibiting IN enzymatic activity have been extensively described in the art. Indeed, as a result of the identification of LEDGF/p75 as a cofactor of HIV IN for the tethering and correct integration of the viral genome into the host chromatin (Cherepanov et al., 2003; Debyser et al., 2015 for a detailed review) the LEDGF/p75-IN interaction became an attractive antiviral target for the treatment of retroviral infections such as HIV/AIDS. This has led to the development of antiviral compounds, the activity of which is based on the inhibition of this interaction (Christ et al., 2010 above). It has been established in this regard that in the absence of LEDGF/p75, HRP2 determines HIV integration sites. LEDGINs thus also inhibit the interaction between HRP-2 and Integrase (Schrijvers et al., 2012).

The interaction or interference, such as inhibition, of a compound with binding of retroviral IN to LEDGF/p75 can be determined by a protein-protein interaction assay as known in the art, including, but not limited to, the AlphaScreen assay, a Homogeneous Time Resolved Fluorescence (HTRF) assay, a pull down assay, thermophoresis and the Biacore® system.

The compounds envisaged herein are compounds also referred to as "LEDGINs", i.e. small molecule inhibitors binding to the LEDGF/p75 binding pocket of HIV-integrase and inhibiting LEDGF/p75-IN protein-protein interaction. The binding of the compounds envisaged herein to HIV-integrase can be determined by a binding assay as known in the art, including, for example but without limitation, a calorimetric binding assay, the Biacore® system, nuclear magnetic resonance (NMR) systems, and by crystallography. While the effect of these compounds was anticipated to be essentially based on the blocking of retroviral integration at the infection stage, an additional impact of these compounds at a later stage of replication, namely viral particle maturation, has also been reported (Jurado et al., 2013 above).

A review of the patent literature on LEDGINs is provided in Demeulemeester et al. (Demeulemeester et al., 2014). Examples of compounds as envisaged for use in the methods provided herein include those disclosed in Demeulemeester al. and the documents referred to therein such as but not limited to thieno [2,3-b] pyridine derivatives described in WO2010130842, pyrimidine derivatives described in WO2011015641, the anti-viral compounds disclosed in WO2012065963 and including more particularly 2-(quinolin-3-yl)acetic acid derivatives such as 2-(6-chloro-2-methyl-4-phenylquinolin-3-yl)pentanoic acid or "CX014442" (Christ et al., 2010).

Methods for the development of compounds capable of interfering with the binding of retroviral IN to LEDGF/p75 have been described in the art. Indeed, Christ et al. (Christ et al., 2010, above) describes the rational design of small-molecule inhibitors of the LEDGF/p75-integrase interaction and HIV replication. In brief, an extensive library of compounds were first filtered based on chemo-informatical rules defining chemical properties of small-molecule inhibitors of protein-protein interactions. The remaining compounds were then screened against a pharmacophore model (based on the crystal structure of the IBD-IN complex, to select compounds having features compatible with the LEDGF/p75-binding pocket. In a next step, the remaining molecules were docked into the binding pocket (reconstructed from the 1HYV crystal structure) using appropriate software package. The 25 most promising compounds were retained for biological evaluation (i.e. inhibition of LEDGF/p75-IN binding and antiviral effect) after which chemical analogs were also obtained and screened. The 2-(quinolin-3-yl) acetic acid derivatives were identified in this way.

The application provides LEDGINs, i.e. compounds capable of interfering with the binding of retroviral IN to LEDGF/p75, for use in curing patients suffering from retroviral infections. The term "curing" or "curative treatment" is used herein to refer to the fact that active viral replication does not resume after cessation of treatment. Indeed, a person is considered cured when he has achieved what is known as a sustained virologic response (SVR), or continuation of this undetectable status, 12 to 24 weeks after completing therapy. Thus, curing or curative treatment in the context of the present invention, means that the LEDGINs/treatment ensures that the viral reservoir established cannot be reactivated, thereby effectively providing a remission of the retroviral infection.

It is noted that LEDGINs as such are antivirals that already reduce the build-up of a viral reservoir upon infection. Without wanting to be bound by theory, it is considered that in the context of the present invention, the residual retroviral reservoir is modified as a result of the administration of the compounds as envisaged herein. LEDGINs ensure retargeting of the viral integrants in such a way that they can no longer be reactivated to actively replicating viruses.

The methods of the present invention are thus characterized in that they envisage administering the compounds described herein for a limited time. This is in contrast to the current medication strategies wherein a continuous or chronic treatment regimen is used to continuously suppress the retroviral infection. More particularly, it is envisaged that the compounds are administered for a period of time until the retroviral reservoir of said animal is resistant to reactivation. The reactivation potential of the retroviral reservoir can be determined by measuring the proviral load, which can be assessed by a qPCR method, revealing the number of proviruses, or by a Viral Outgrowth Assay, revealing the number of functional proviruses. Preferably, the Viral Outgrowth Assay is used. In particular embodiments of the methods described herein, it is envisaged that the compound is administered for a period of time until the proviral load becomes undetectable. In further particular embodiments, the compound is administered for a predetermined time period of between 1-24 weeks, after which the reactivation potential of the retroviral reservoir is determined, based on which it is decided whether or not to continue administration of the compound, as will be detailed below.

Accordingly, provided herein are methods of curing a retroviral infection in an animal comprising the administration of a compound capable of binding to the LEDGF/p75 binding pocket of HIV-integrase and inhibiting LEDGF/p75-IN protein-protein interaction as described herein and determining the reactivation potential of the retroviral reservoir in said animal. In particular embodiments, the reactivation potential of the retroviral reservoir is determined by measuring the proviral load in said animal. Based on this determination of the reactivation potential, it can be determined whether or not the animal has been cured or whether treatment should be continued. In these methods, the cut-off value for determining whether or not the reactivation potential has been suppressed is typically the detection limit of the assay. In particular embodiments of the methods provided herein, the duration of administration is determined based on the reactivation potential of the retroviral reservoir as determined after a first treatment regimen. Indeed, where the reactivation potential is low or non-existent, the treatment can be stopped. Where the reactivation potential has not been completely suppressed, the treatment can be continued.

In particular embodiments, the methods of the present invention involve a treatment regimen of less than 12 months, more particularly less than 6 months, more particularly less than 24 weeks, more particularly less than 4 months, more particularly less than 3 months or 12 weeks, most particularly between 1 to 8 weeks, such as for 6 weeks. In particular embodiments, the time period of the first treatment regimen prior to detection of the viral load is between 1-24 weeks, whereby, if remission is not established, the compound is administered for a second discrete time period of 1-24 weeks. Accordingly these time periods are envisaged as discrete time periods, implying that, once remission is established, the treatment is stopped thereafter. Most particularly this implies that no other anti-retroviral therapy is administered thereafter. In view of the above it will be understood that in preferred embodiments of the methods described herein, the treatment does not need to be repeated and the treatment regimen consists only of the administration of the compounds envisaged herein within the indicated time frame. It can be envisaged however that in particular embodiments, 1, 2 or even 3 additional treatment regimens may be necessary, if the first treatment regime was not sufficiently effective to ensure the desired effect, i.e. complete retargeting of viral integrants, or if, after a prolonged period of time (e.g. 2-5 years), there is nevertheless a resurgence of the viral infection. However, the consecutive administration of the herein described treatment regimen to the same patient more than three times, more particularly within a time period of 3 years is not envisaged to be within the scope of the present application.

The efficacy of the curative treatment as provided herein can be determined by assaying the reactivation ability of the viral reservoir of the patient during or after the treatment with LEDGINs. More particularly this can be assessed by the viral outgrowth assay on blood samples taken from the patient.

An exemplary protocol for the viral outgrowth assay is described e.g. in Laird et al. (PLoS Pathog. 2013; 9 (5): e1003398). Typically, CD4+ T lymphocytes obtained from a single blood draw are used. Briefly, serial dilutions of resting CD4+ T lymphocytes from HIV-1 infected patients are stimulated by co-culture with a 10-fold excess of γ-irradiated allogeneic PBMC from uninfected donors and the mitogen PHA (Remel) in RPMI containing 10% fetal bovine serum, 100 U/mL IL-2 and 1% T-cell growth factor. These conditions are sufficient to activate 100% of the resting CD4+ T lymphocytes. T cell activation reverses HIV-1 latency in at least a fraction of the latently infected cells. After one day of stimulation, the mitogen containing media is removed and either MOLT-4/CCR5 cells or health donor CD4+ lymphoblasts are added in fresh media to propagate replication-competent HIV-1 in the culture wells. The standard viral outgrowth assay utilizes two additions of CD4+ lymphoblasts from uninfected donors as target cells for HIV-1 outgrowth on days 2 and 9. The MOLT-4/CCR5 viral outgrowth assay utilizes a single addition of MOLT-4/CCR5 cells on day 2. The ratio of target cells added is the same for both assays. For instance, $1 \times 10^7$ target cells are added to wells containing $1 \times 10^6$ patient resting CD4+ T cells and $2.5 \times 10^6$ target cells are added to all other wells. Five days after initial mitogen stimulation of input resting CD4+ T lymphocytes, the culture media is changed and the cells in each well are split. Supernatants from each well are tested for HIV-1 RNA and/or HIV-1 p24 protein at various time points by RT-PCR and ELISA, respectively. The frequency of latently infected cells among the input resting CD4+ T lymphocytes is calculated by a maximum likelihood method, and is expressed as infectious units per million cells (IUPM).

In the viral outgrowth assay, virus replication is measured (eg by p24 ELISA) after reactivation of blood cells. Curative treatment will reduce the ability for reactivation. Accordingly, in particular embodiments, it is envisaged that this assessment can be used to either determine during the course of treatment with LEDGINs, whether treatment is effective, in order to determine whether or not treatment with LEDGINs can be stopped. Additionally or alternatively it is envisaged that this assessment can be used to determine, after treatment with LEDGINs has been stopped, whether or not the treatment has been effective and a functional cure has been achieved. Additionally or alternatively, this can be used to determine, at one or more time points at one or more extended time points after treatment, such as after a time period of 5 years, whether there is any risk of reappearance of the infection (which would be caused by proliferation of a limited amount of virus which had escaped the retargeting by LEDGIN treatment).

Additionally or alternatively, retargeted provirus integration sites can be determined in patient blood lymphocytes to determine treatment efficacy. Again this can be performed during or after the treatment regimen.

Additionally or alternatively, after cessation of LEDGIN treatment, functional cure or remission of the patient can be assessed by determining, in the absence of any antiretroviral therapy, the viral load or the DNA proviral load, preferably the DNA proviral load. Accordingly it is envisaged that in particular embodiments the methods may include the step of determining the viral load or DNA proviral load in a sample of said patient at least once and preferably at several time points within 2-12 weeks e.g. 3, 8 and 12 weeks after cessation of the treatment regimen.

As detailed above, further follow-up monitoring can of course also be envisaged at later time-periods. In particular embodiments, viral load or DNA proviral load is determined upon cessation of LEDGIN treatment and after 2-12 weeks and confirmation of the curative treatment or remission is obtained when the viral load or DNA proviral load is not increased compared to that determined upon cessation of LEDGIN treatment. Methods for determining the retroviral titer in a sample of the patient are known in the art and include but are not limited to the quantification of viral genomes through quantitative PCR methods (DNA proviral load) and quantification of the presence of the viral protein p24 through ELISA (viral load). Exemplary protocols are described in the examples.

It is envisaged that in order to ensure the desired effect, the compounds capable of interfering with the binding of retroviral IN to LEDGF/p75 envisaged for use herein are administered at a dosage comparable to or at an increased dosage, preferably at a comparable dosage, compared to the dosage of the drug as would be envisaged for standard anti-retroviral therapy. Indeed, it has been observed herein that in particular embodiments, the concentration of LEDGIN used to ensure the retargeting effect is significantly higher than the concentration of the compound used to block virus replication in cell culture. In alternative embodiments however, the concentration of LEDGIN used is comparable to that used in standard treatment.

Typically, dosage of a drug is based on the half-maximal effective concentration (EC50), i.e. the concentration of the drug at which it ensures 50% of its maximal effect. In the context of anti-retroviral drugs, this typically corresponds to the concentration of a drug needed to block viral replication by 50% in an in vitro cell culture. In some instances, the EC90 value is considered relevant, i.e. the concentration of a drug needed to block viral replication by 90%. In the literature, "IC50" (the half-maximal inhibitory concentration) is sometimes used for the effect of a compound on viral replication in cell culture, such that these terms appear interchangeable. As the inhibitory concentration of a compound in principle refers to the inhibition of enzymatic activity, preference is given herein to use the antiviral EC50 value to refer to the concentration of the compound required to ensure 50% of the antiviral effect in vitro.

The concentration of a LEDGIN required for achieving reintegration can be equal or higher than the concentration required for ensuring inhibition of viral replication. Generally it is envisaged that the EC50 of a LEDGIN for achieving a functional cure is equal or higher than the antiviral EC50 of said LEDGIN, such as at least 2×, 5×, 10×, such as 20×, 50×, 100×, 200× or 500× or more the antiviral EC50 value.

The dosage of the compounds for use in the methods described herein is based on the estimated concentration of the compound required to ensure a functional cure or remission. More particularly, the dosage can aim to ensure a trough concentration in the blood of at least the concentration required for a functional HIV cure. In particular embodiments, the dosage ensures that the trough concentration in the blood of the patient is the same or higher, such as 2× or 3× higher than the concentration of the compound required for ensuring retargeting in vitro.

In order to ensure that the compounds as envisaged herein can optimally exert their retargeting effect, it is thus envisaged that the concentration of the compound in the blood of the patient is equal or higher than the concentration required for its antiviral effect in standard therapy. More particularly, the dosage is envisaged to be equal or two, three, four, five or up to 10, 100, 200, 300 or even 500 times higher than the dosage of the drug envisaged for standard therapy, or any value there between.

It is envisaged that in particular embodiments of the methods provided herein the compound is administered in a once a day or more than once a day. An administration scheme of more than once a day may be particularly advantageous for compounds with less favorable pharmacokinetics. The compound may also be administered more than once a day to ensure a high concentration of the compound in the patient's body. It is envisaged that in particular embodiments, the dosage may exceed the dosage for the Cmax, i.e. the dosage whereby short-term side effects are experienced by the patient. However, in view of the limited duration of the treatment, these side-effects will be considered more tolerable than when considered for continuous, life-long therapy.

The methods provided herein are based on the effect of compounds which are able to interfere with the LEDGF/p75-IN interaction on retargeting of viral integrants. In order to ensure this effect, administration of the compound during active replication and integration of the virus is necessary. Accordingly, in particular embodiments, the patient is a treatment-naïve HIV-infected patient. In particular embodiments, the patient has a detectable viral load, as this is indicative of active replication. Methods for determining viral load are known in the art and include detection of viral RNA and detection of antibodies directed against the virus.

In alternative embodiments, the patient is a patient which has previously received antiretroviral therapy. Such antiretroviral therapy can be monotherapy or combination therapy with one or more drugs such as but not limited to nucleoside reverse transcriptase inhibitors (NRTI), other non-nucleoside reverse transcriptase inhibitors, protease inhibitors or fusion inhibitors. More particularly, the patient may previously have received standard therapy, i.e. a combination therapy of at least two, preferably three different types of anti-retroviral drugs. In these embodiments however it is envisaged that the patient is preferably a patient for which this treatment has been interrupted. Accordingly, the methods as envisaged herein may encompass interrupting said antiviral therapy prior to the administration of the compound envisaged herein. In particular embodiments, the prior treatment is interrupted for at least 5 days, preferably at least 7 days or more prior to administering the compound, as envisaged herein.

Accordingly, in particular embodiments, a patient undergoing standard antiretroviral therapy under chronic cART, with undetectable levels of circulating HIV in the blood, can be treated as envisaged herein, whereby the previous treatment is interrupted to induce a viral rebound which is then treated with a short course of LEDGINs, eg. by using a standard or an acute dosage regimen, to retarget integration and to induce or enhance the silent reservoir.

The above implies that LEDGINs can be used for late stage infections by first allowing the virus to rebound, e.g. by cessation of standard therapy, and then starting with a curative therapy as envisaged herein wherein the LEDGIN is typically used in an acute dosage regimen.

It is envisaged that the methods provided herein can involve the administration of the compounds interfering with the LEDGF/p75-IN interaction with other anti-viral drugs which are aimed at reducing the viral load, examples of which are provided below. More particularly, in particular embodiments, the methods provided herein encompass combining the administration of the compound as envisaged herein with the administration of a protease inhibitor (PI). Indeed, it is envisaged that as protease inhibitors act in a phase which is later than the integration step, the concomitant administration of protease inhibitor is less likely to affect the efficacy of reintegration.

In particular embodiments however, the methods provided herein envisage the administration of the compound capable of interfering with the LEDGF/p75-IN interaction as a monotherapy. Indeed, as the compounds envisaged for use herein have an effect both on the retargeting of viral integrants and on viral replication, the advantage of combination with other drugs for a functional cure may be limited and the combination with specific types of anti-retrovirals, more particularly those that interfere with early replication steps ((entry, reverse transcription, integration) may negatively affect the effect of LEDGINs on retargeting integration. Moreover, administering the compounds as envisaged herein as a monotherapy may further increase the tolerance by the patient of an increased dose and/or reduce the risk of accumulation of undesirable side-effects.

Nevertheless, as indicated above, in particular embodiments it may be of interest, to administer a compound capable of interfering with the LEDGF/p75-IN interaction in combination with other agents, including other compounds as envisaged herein. Certain compounds may be effective for enhancing the biological activity of other agents by reducing the metabolism, catabolism or inactivation of other compounds and as such, are co-administered for this intended effect.

Compounds which have been described in the art as being useful for the treatment of HIV including those presently used to treat HIV such as HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gpl20 inhibitors, CCR5 inhibitors, capsid polymerization inhibitors, fusion inhibitors, including anti-HIV compounds presently in clinical trials or in development and other drugs for treating HIV, and combinations thereof.

Exemplary compounds of the above include, for example, 3TC (Lamivudine), AZT (Zidovudine), (–)-FTC, ddl (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), ETR (etravirine), Edurant (rilpivirine), SQVM (Saquinavir mesylate), RTV (Ritonavir), IDV (Indinavir), SQV (Saquinavir), NFV (Nelfinavir), APV (Amprenavir), LPV (Lopinavir), T20, and fuseon among others. These compounds may be used in combination with the compounds envisaged for use in the methods of the present application for their additive activity or treatment profile against HIV and/or other viruses and in certain instances, for their synergistic effects in combination with compounds capable of interfering with the LEDGF/p75-In interaction. Accordingly, in particular embodiments, methods are provided for curing a retroviral, more particularly an HIV infection in a mammal (e.g., a human) comprising administering to the mammal in need thereof a curative dosage of a LEDGIN, or a pharmaceutically acceptable salt thereof, in combination with a therapeutically effective amount of one or more additional therapeutic agents described above. In a more particular embodiment, said one or more additional therapeutic agents are protease inhibitors.

The application thus provides methods for curing a retroviral infection, such as an HIV infection, comprising administering to a patient in need thereof a curative amount of a LEDGIN or a pharmaceutically acceptable salt, thereof. The application further provides pharmaceutical compositions comprising a LEDGIN, or a pharmaceutically acceptable salt thereof, in a curative dosage as envisaged herein and a pharmaceutically acceptable carrier. The application provides the pharmaceutical compositions as envisaged herein packaged so as to allow the administration of a curative dosage regimen.

The LEDGINS as envisaged for use herein are formulated with conventional carriers (e.g., inactive ingredient or excipient material) which are selected by the skilled practitioner. Tablets can be provided containing excipients one or more of fillers, binders and the like. Aqueous formulations are prepared in sterile form, and are preferably isotonic when envisaged for intravenous administration. The formulations may comprise excipients such as, but not limited to ascorbic acids, chelating agents such as EDTA, carbohydrates such as dextrin, hydroxyalkylcellulose, hydroxyalkylmethylcellulose, and/or stearic acid. Suitable excipients are known to the skilled person (Handbook of Pharmaceutical Excipients (1986)). pH of the formulations is typically between 3 and 11.

The nature of the formulation will depend on the envisaged route of administration. For oral administration, typically formulation of discrete units is provided in capsules, cachets or tablets each containing a predetermined amount of the active ingredient. Alternatively oil suspensions, dispersible powders or granules, emulsions, or syrups can also be envisaged. For oral preparations, the formulation may further comprise sweetening, flavoring or coloring agents.

Where applicable, the amount of active ingredient per dosage unit will be determined, inter alia, based on the activity, more particularly the EC50 (also sometimes corresponding to the IC50) of the relevant LEDGIN against spreading HIV-1 infection in cell culture. Typically, a dosage form for oral administration to humans contains between 1 to 1000 mg of active ingredient formulated with the appropriate excipient material. In certain embodiments, the carrier material represents between 5 to about 95 weight % of the total composition.

The EC50 represents the concentration of a drug that is required for 50% inhibition of viral replication in an vitro cell culture.

The EC50 of a compound, i.e. the concentration of a drug needed to inhibit viral replication by 50% in cell culture can be determined as follows.

An HTLV-1 transformed T4-cell line MT-4 (Pauwels et al., 1988), which has been shown to be highly susceptible to and permissive for HIV infection, serves as the target cell line. Inhibition of the HIV-induced cytopathogenic effect is used as the end point. The viability of both HIV- and mock-infected cells is assessed spectrophotometrically.

Briefly 3-fold serially diluted compounds in DMSO are added to 40 µl of cell growth medium (e.g. RPMI 1640, 10% FBS, 1% penicillin/Streptomycin, 1% L-Glutamine, 1% HEPES) in each well of a multiwell assay plate (10 concentrations) in quadruplicate.

1 mL aliquots of 2×10e6 MT-4 cells are pre-infected for 1 and 3 hrs respectively, at 37° C. with 25 µï, (MT4) or of either cell growth medium (mock-infected) or a fresh 1:250 dilution of an HIV concentrated ABI stock (0.004 m.o.i. for MT4 cells). Infected and uninfected cells are diluted in cell growth medium and 35 \iL of 2000 (for MT4) cells is added to each well of the assay plates. Assay plates are then incubated in a 37° C. incubator. After 5 days of incubation, an agent suitable for chemoluminescent detection of viability is added to each well of the assay plate. Cell lysis is carried out by incubating at room temperature for 2-3 min and then chemiluminescence is read spectophotometrically. Examples of suitable reagents include but are not limited to MTT based reagents or ATP-based reagents (e.g. CellTiter-Glo® Assay).

The LEDGINs for use as envisaged herein may be administered by different routes including oral, rectal, nasal, topical (including buccal and sublingual), vaginal and parenteral (including subcutaneous, intramuscular, intravenous, intradermal, intrathecal and epidural), and the like. In particular embodiments, the administration is oral.

The methods are envisaged herein for treatment of a retroviral infection in an animal, more particularly a mammal, such as but not limited to a human.

In a second aspect, the present application provides safer methods for gene therapy, in particular retroviral gene therapy. Indeed, the possibility of oncogenic transformation of host cells as a result of integration of retroviral DNA into a "wrong spot" of the host chromosome has always been a concern. The present inventors have found that compounds capable of interfering with the binding of lentiviral IN to LEDGF/p75 (also referred to as LEDGINs) retarget integration of retroviruses towards safe sites. Accordingly, appropriate administration of LEDGINs as envisaged herein ensures retargeting of retroviral vector integration towards a "safe site" in the host genome, thereby effectively providing safer retroviral gene therapy. With a "safe site" is meant herein a site in the host cell genome where the integrated material is adequately expressed without perturbing endogenous gene structure or function. Within the context of the present invention, integration of the retroviral vector into the host cell genome is considered "safe" if the following five criteria are met: (i) distance of at least 50 kb from the 5' end of any gene, (ii) distance of at least 300 kb from any cancer-related gene, (iii) distance of at least 300 kb from any microRNA (miRNA), (iv) location outside a transcription unit and (v) location outside ultra-conserved regions (UCRs) of the human genome. Additionally or alternatively, a site can be identified as "safe" if it is recognized to be a site which does not lead to clonal proliferation or malignancy.

The application thus provides for the use of compounds capable of interfering with the binding of retroviral IN to LEDGF/p75 in methods for introducing a genetic modification, such as the delivery of a transgene, in a cell with a retroviral vector. The compounds envisaged for use herein are capable of binding to the LEDGF/p75 binding pocket of HIV-integrase and compete with wild-type LEDGF/p75 for binding to HIV integrase thereby inhibiting LEDGF/p75-IN protein-protein interaction and suppressing the function of LEDGF/p75.

Accordingly, also disclosed herein is the use of a compound capable of interfering with the binding of retroviral IN to LEDGF/p75, such as a LEDGIN, as described herein in combination with a retroviral vector, preferably a lentiviral vector, such as a HIV-1-based vector, for introducing a genetic modification into a cell. In particular embodiments, the method of genetic modification is carried out on a cell in vitro or ex vivo.

Further disclosed herein is an in vitro or ex vivo method for delivering a transgene into a host cell comprising contacting said host cell with a retroviral vector preferably a lentiviral vector, such as a HIV-1-based vector, comprising said transgene and a compound capable of interfering with the binding of retroviral IN to LEDGF/p75 as described herein. Said method may further comprise determining the integration site of said transgene in said host cell, and optionally selecting the host cells in which said transgene has been integrated in a safe genomic location.

The application further provides ex vivo and in vivo methods of gene therapy with a retroviral vector in a subject, which methods comprise administering to a cell of said subject a compound capable of interfering with the binding of retroviral IN to LEDGF/p75 as described herein, in combination with said retroviral vector. Also disclosed herein is a compound which is capable of interfering with the binding of retroviral IN to LEDGF/p75 as described herein for use in a method of gene therapy with a retroviral vector in a subject, whereby said method comprises contacting a cell of said subject with said compound and said retroviral vector. Retroviral gene therapy uses retrovirus-derived vectors for modifying the genome of a host cell, such as, but not limited to by delivering a transgene into a host cell. Retroviruses are RNA viruses that have the ability to insert their genes into host cell chromosomes after infection. Retroviral and lentiviral vectors have been developed that lack the genes encoding viral proteins, but retain the ability to infect cells and insert their genes into the chromosomes of the target cell. The difference between a lentiviral and a classical Moloney-murine leukemia-virus (MLV)-based retroviral vector is that lentiviral vectors can transduce both dividing and non-dividing cells whereas MLV-based retroviral vectors can only transduce dividing cells. Accordingly, in the methods and uses envisaged herein the retroviral vector is preferably a lentiviral vector.

Lentiviruses include members of the bovine lentivirus group, equine lentivirus group, feline lentivirus group, ovine-caprine lentivirus group and primate lentivirus group. The development of lentiviral vectors for gene therapy has been reviewed by Tomás et al. (2013, Chapter 12, pages 287-317 in Biochemistry, Genetics and Molecular Biology: "Gene Therapy—Tools and Potential Applications" edited by Francisco Martin Molina, ISBN 978-953-51-1014-9). The design and use of lentiviral vectors suitable for gene therapy is described, for example, in U.S. Pat. Nos. 6,207,455, and 6,165,782. Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus. Preferably, the lentivirus is a human immunodeficiency virus (HIV), such as HIV-1.

The retroviral vectors envisaged herein typically comprise a nucleic acid sequence or transgene operably linked to a promoter. For example, the nucleic acid sequence may encode a secretable protein or a protein which is defective in the host cell, or ensure disruption of a defective gene in the host cell.

Other sequences may be incorporated in the retroviral vectors envisaged herein as well, typically to further increase or stabilize the expression of the transgene product (e.g. introns and/or polyadenylation sequences). The promoter does not need to be the promoter of the transgene in the viral vector, although it is possible that the transgene is transcribed from its own promoter. The promoter may be homologous (i.e. from the same species as the subject to which the retroviral vector is administered) or heterologous (i.e. from a source other than the species of the subject to which the retroviral vector is administered). The promoter may be an inducible or constitutive promoter.

The retroviral vectors envisaged herein may be configured to enhance expression levels of the transgene comprised in the vector. This can be achieved by appropriate vector design, including the use of cis-acting elements such as promoters, introns, post-transcription regulatory elements such as WPRE, polyadenylation signals, and the CMV enhancer as known in the art (Powell et al. 2015). Retroviral vectors ensuring high transgene expression may be particularly useful for compensating for the reduced integration induced by certain compounds envisaged herein. Indeed, certain LEDGINs inhibit the integration activity of IN, thereby inhibiting the transduction efficiency of the retroviral vector which is administered or introduced in combination with the LEDGIN.

The transgene that may be contained in the retroviral vectors envisaged herein typically encodes a gene product such as RNA or a polypeptide (protein). Those skilled in the art will appreciate a variety of transgenes that are suitable for use with the invention. In embodiments, the transgene encodes a therapeutic protein. Non-limiting examples of therapeutic proteins include clotting factors, such as factor VIII or factor IX, insulin, erythropoietin, lipoprotein lipase, antibodies or nanobodies, growth factors, cytokines, chemokines, plasma factors, etc. For example, the transgene may encode an immunogenic protein. Non-limiting examples of immunogenic proteins include epitopes and antigens derived from a pathogen.

It is envisaged that the retroviral gene therapy methods envisaged herein can be applied e.g. to express a therapeutic amount of a transgene product (such as a polypeptide, in particular a therapeutic protein, or RNA) for therapeutic purposes, to express a prophylactically effective amount of a transgene product to prevent the onset of a disease or disorder, or to express an immunological amount of a transgene product (such as a polypeptide, in particular an immunogenic protein, or RNA) for vaccination purposes. Exemplary diseases and disorders that may benefit from the retroviral gene therapy described herein include genetic disorders (such as hemophilia, including hemophilia A and B, β-thalassemia, muscular dystrophy (e.g. Duchenne muscular dystrophy (DMD)), diabetes, cancer, infectious diseases or other condition.

Alternatively, the retroviral gene therapy methods envisaged herein can be applied to disrupt a defective gene. The gene therapy methods envisaged herein may for example introduce elements which ensure DNA editing, using techniques such as zinc finger nucleases and CRISPR. The vector incorporates genes encoding the elements required for editing into chromosomes and these elements then edit the relevant chromosome in a specific way.

The delivery of a transgene into a host cell may be performed ex vivo or in vivo. The ex vivo approach requires harvesting of the host cells from a subject, in vitro transduction of the host cells with a retroviral vector comprising the transgene, and re-introduction of the transduced host cells into the subject. The in vivo approach requires the administration of a retroviral vector comprising the transgene directly to a subject. The retroviral gene therapy envisaged herein may be in vivo gene therapy or ex vivo gene therapy.

Accordingly, the methods provided herein may involve contacting a host cell with a retroviral vector comprising a transgene and with a compound which competes with wild-type LEDGF/p75 for binding to retroviral integrase. Where it is envisaged that the host cell is contacted with the retroviral vector ex vivo, the host cell may be part of an isolated host cell population (e.g. blood or a fraction thereof) or an isolated tissue or organ. Thus the methods described herein may comprise the step of providing a host cell. While this step is not critical, the herein described methods may further involve isolating the host cell from the host.

Where it is envisaged that the host cell is contacted with a retroviral vector in vivo, these methods encompass administering the retroviral vector to the patient comprising said host cell. The retroviral vector may be delivered in vivo to the subject in a formulation or a pharmaceutical composition with a pharmaceutically acceptable carrier, i.e., one or more pharmaceutically acceptable excipients and/or additives, e.g., buffers, carriers, excipients, stabilizers, etc. The term "pharmaceutically acceptable" as used herein is consistent with the art and means compatible with the other ingredients of a pharmaceutical composition and not deleterious to the recipient thereof.

In vivo gene therapy protocols have been extensively described in the art. These include, but are not limited to, intramuscular injection, microinjection, hydrodynamic gene delivery in various tissues, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure.

The application thus provides a lentiviral vector for use in a method of gene therapy, characterized in that the lentiviral vector is co-administered with a compound capable of interfering with the binding of lentiviral IN to LEDGF/p75.

Methods of determining the most effective means and dosage of retroviral vector administration are well known to those of skill in the art and will vary with the vector used for therapy, the purpose of the therapy, the host cell being treated, and the subject being treated.

The methods envisaged herein involve contacting the host cell with relatively high titers of retroviral vector, either ex vivo or in vivo in order to compensate for the negative effect of the compounds on integration efficiency. Where the method is an in vivo gene therapy method, this can be ensured by administering a similar or higher dosage of the retroviral vector than would be administered in a method not involving the administration of the compounds envisaged herein. For example, the dosage of the retroviral vector may be the same or at least 2×, more particularly at least 5×, or 10× or more the dosage that would normally be envisaged. It is noted that where the method involves contacting the cells with the retroviral vector ex vivo, the amount of retroviral vector used can be increased.

The methods provided herein are based on the effect of the compounds envisaged herein to retarget integration of the retroviral vector. In order to ensure this effect, contacting of the host cell with the compound during integration of the retroviral vector is necessary. Accordingly, in the methods envisaged herein, the compound capable of interfering with the binding of retroviral IN to LEDGF/p75 is used in combination with the retroviral vector. Generally, this is referred to as co-administration, though this does not require that the viral vector and the compound are administered together or simultaneously as will be apparent from the passages below.

Where the method is a method of in vivo gene therapy, this implies the administration of both the compound and the retroviral vector. The compound and the retroviral vector may be administered in either the same or different pharmaceutical formulation(s), simultaneously or sequentially, with the compound being preferably administered first. For example, the compound may be administered initially followed by administration of the retroviral vector within 24 hours, preferably within 12 hours, more preferably within 8 hours such as within 6 hours, 4 hours or 2 hours, even more preferably within 1 hour.

Where the host cell is contacted with the retroviral vector in vitro or ex vivo, the method can comprise contacting the host cell with the compound capable of interfering with the binding of retroviral IN to LEDGF/p75 and with the retroviral vector simultaneously. Alternatively, the host cell may be contacted with the compound prior to being contacted with the retroviral vector. More particularly the host cell may be contacted with the compound first, whereafter the host cell is contacted with the vector within 24 hours, preferably within 12 hours, more preferably within 8 hours such as within 6 hours, 4 hours or 2 hours, even more preferably within 1 hour.

The dosage or amount of the LEDGIN to be used in the methods provided herein can be established by the skilled person. The optimal dosage or amount will be the dosage which ensures retargeting of the retroviral vector but at the same time has an acceptable effect on the integration efficiency.

It is envisaged that in order to ensure the desired effect of retargeting integration of the retroviral vector, the amount of the compound used in the methods provided herein is at least the amount known to suppress spreading retroviral replication in cell culture, such as the amount known to suppress spreading retroviral replication in cell culture or an amount that is at least twice as high, more particularly at least 5×, 10×, 100× or 500× as the amount known to suppress spreading retroviral replication in cell culture. The EC50 of the compound to ensure safe targeting of the retroviral DNA can be first determined in vitro. This can be used as a basis to determine suitable dosage for in vivo administration by the skilled person. As detailed above, the negative effect on retroviral integration by the compounds envisaged herein can be compensated by increasing the efficiency of expression of the retroviral vector (e.g. the use of enhancers etc.) and/or by further increasing the absolute amount of the retroviral vector (and compound) with which the host cell is contacted. The latter is particularly suited for methods of ex vivo gene modification, where toxic effects are less relevant. More particularly in ex vivo methods, the method may involve selecting those cells where the desired effect of the methods envisaged herein has been achieved.

The efficacy of the compounds to ensure targeting of the retroviral DNA into safe sites can be determined by determining the integration sites in the host cell. Where the host cell is contacted with the retroviral vector in vitro or ex vivo, the method may comprise selecting the cells wherein the retroviral vector has been integrated in "safe" sites. Only those cells where the transgene has been introduced in the desired regions can then be selected for further use, e.g. for administration to the patient.

For in vivo administration the compounds envisaged herein are typically formulated into pharmaceutical compositions or formulations with one or more pharmaceutically acceptable carriers (e.g., inactive ingredient or excipient material) for ease of administration.

For in vivo gene therapy methods the compounds envisaged herein may be administered by different routes including oral, rectal, nasal, topical (including buccal and sublingual), vaginal and parenteral (including subcutaneous, intramuscular, intravenous, intradermal, intrathecal and epidural), and the like. In particular, the administration may be intravenous or by local injection, infusion, electroporation or implant.

It has been established that local gene therapy offers significantly enhanced transfection efficiency with decreased toxicity compared to system delivery. It will be understood to the skilled person that where local gene therapy is envisaged, administration of LEDGIN should ideally also be local. Accordingly, the methods envisaged herein may involve local administration of the LEDGIN and retroviral vector.

The nature of the formulation will depend on the envisaged route of administration. For local administration the active ingredient is typically formulated as a liquid composition and may be provided on a carrier (nanoparticle). Implants may be provided which retain the active ingredient to ensure sustained delivery.

Alternatively for oral administration, typically formulation of discrete units is provided in capsules, cachets or tablets each containing a predetermined amount of the active ingredient. Alternatively oil suspensions, dispersible powders or granules, emulsions, or syrups can also be envisaged. For oral preparations, the formulation may further comprise sweetening, flavoring or coloring agents.

The methods are envisaged herein for genetic modification of a host cell of an animal, more particularly a mammal, such as but not limited to a human.

The invention will be illustrated by the following non-limiting examples.

EXAMPLES

Example 1

LEDGF/p75 Depletion Increases the Size of the Latent Reservoir

The effect of LEDGF/p75 and LEDGF/p75-mediated integration site selection on the establishment of the latent reservoir was determined by the use of a variant of the recently developed double reporter virus that simultaneously measures a constitutive and a LTR-driven reporter (see M&M below) (Calvanese et al., 2013). This orange-green HIV-1 (OGH) single-round reporter virus encodes a LTR-driven enhanced Green Fluorescent Protein (eGFP) together with a constitutively active EF1alpha promoter driving mutant Kusabira-Orange2 (mKO2) expression (FIG. 1A). This double-fluorescent reporter virus allows direct visualization via FACS analysis of distinct populations in the infected cell pool: all infected cells express the mKO2 reporter protein; viruses that have an active LTR also express the eGFP reporter (this population is referred to as double positive, active proviruses), whereas proviruses with an inactive LTR do not express eGFP (i.e. the latent provirus pool) (FIG. 1B).

Wild type SupT1 cells and SupT1 LEDGF/p75 KD cells were infected with a dilution series of single-round OGH reporter virus. The percentage of infected cells was evaluated at three days post infection distinguishing productively infected cells (active provirus; eGFP+/mKO2+) and latently infected cells (quiescent provirus; eGFP−/mKO2+) populations. As expected, infection of LEDGF/p75 depleted cells resulted in a reduced infection as judged by the % mKO2 positive cells (data not shown). In addition HIV infection of these cells resulted in 2-3 fold more quiescent cells than in WT cells (FIG. 1C). Similar data were obtained when evaluating the cells at 7 days post infection indicating that the reporter expression originates from integrated provirus (data not shown). The experiment was also performed in the in house generated Nalm LEDGF/p75 KO cells where a comparable 2-fold increase in the proportion of quiescent cells was seen (Schrijvers et al., 2012 above; data not shown). Also here, we determined provirus integration sites and corroborated altered integration site distribution (data not shown), suggesting that the altered integration site distribution under LEDGF/p75-depleted conditions results in an increased percentage of quiescent cells. The quiescent cells carry integrated proviruses that are either permanently silent or proviruses that are latent and can be re-activated.

2

HIV Infection of Cells Depleted for LEDGF/p75 Results in a Latent Reservoir That Is Resistant to Reactivation The latent provirus was reactivated using different latency reversing agents (LRAs). This was done in the LEDGF/p75 KO cell line (Nalm −/−) (Schrijvers et al., 2012, above). Cells were infected with a NL4.3-based single reporter virus containing the LTR driven truncated tCD34 as a reporter protein (NL4-3.tCD34.R-.E-/VSV-G-, FIG. 2A). Nalm wt (+/c) and Nalm LEDGF/p75 KO (−/−) cells were infected with a HIV tCD34 dilution series. We selected vector dilutions for both the wt and LEDGF/p75 KO containing equal integrated copy numbers in order to compare the fold reactivation between both (data not shown). 11 days post infection cells were reactivated using different LRAs during 24 h (FIG. 2B). We compared the fold reactivation (% tCD34) relative to DMSO for both LEDGF/p75 wt and LEDGF/p75 KO condition. Modest increasing concentrations of tCD34 reactivation were observed after addition of PMA or prostratin. An increase in percentage of tCD34 positive cells of 1.5-2 fold was observed for LEDGF/p75 wt conditions while LEDGF/p75 KO conditions only resulted in an increase of 1.3-1.5 fold when adding Phorbol Myristate Acetate (PMA; 0.3-3 µM) or Prostratin (5 µM) (t test with Sidak-Bonferroni correction; *$p<0.05$, wt compared to LEDGF/p75 KO). Yet, addition of 3 µM Suberoylanilide Hydroxamic acid (SAHA) resulted in a clear reactivation of tCD34 expression (FIG. 2B), with a 3- to 4-fold reactivation in the presence of LEDGF/p75 but only a 2-fold reactivation in the absence of LEDGF/p75 (t test with Sidak-Bonferroni correction; **$p<0.005$, wt compared to LEDGF/p75 KO). Together, these data suggest that integration under LEDGF/p75 depleted conditions results in a larger quiescent cell pool of which a subset is latent and can be reactivated, and a larger proportion of cells is not able to be reactivated, and thus seems permanently silent.

3

LEDGIN Treatment Shifts HIV Integration Out of Transcription Units

In a next step we employed the recently developed LEDGINs, small molecules that inhibit LEDGF/p75-IN interaction and inhibit integration of HIV provirus (Christ et al., 2010, above) to investigate the impact of LEDGIN treatment on the HIV reservoir in cell culture. SupT1 cells were transduced with a single-round HIV-based lentiviral vector expressing the enhanced Green Fluorescent Protein (eGFP) reporter protein and treated with a dilution series of LEDGIN CX014442 (Christ et al 2012, above). Transduction efficiencies were evaluated using flow cytometry monitoring eGFP fluorescence showing a dose-dependent decrease in % eGFP positive cells under LEDGIN treatment (data not shown). In a first step, we determined integration site distribution of HIV-based viral vector integration sites (Gijsbers et al., 2009; Marshall et al., 2007). The number of integration sites is indicated for each data set (Table 1). First, we analysed lentiviral integration relative to a set of genomic features. HIV integration sites in wild-type SupT1 cells were enriched in the body of genes (69.54.0% in RefSeq genes (Table1) disfavoring transcription start sites (TSS) and promoter regions (1.78% within 2 kb of the 5' of a RefSeq gene and 2.02% within 2 kb of a CpG island). The integration sites under LEDGIN-treatment demonstrated a shift out of TUs (54.55% in RefSeq genes (50 µM); *p<0.0001, Chi-square test compared to DMSO) and increased integration close to TSS (6.94% (50 µM); *p<0.0001, Chi-square test compared to DMSO) and CpG islands (5.50% (50 µM); **p<0.01, Chi-square test compared to DMSO) in a dose-dependent manner, phenocopying the pattern observed in LEDGF/p75-depleted cells. Comparable data were observed for larger window sizes (2 kb and 4 kb are shown). These results were corroborated in MT4 using wt HIV NL4-3 and LEDGIN CX05168 (data not shown).

Simultaneously, integration in regions associated with marks common to transcriptionally silent regions or heterochromatin was disfavored (H3K27me3, H3K9me3 or H4K20me3 and H3K79, respectively) (De Ravin et al., 2014), corroborating the preference for open, transcriptionally active chromatin. This epigenetic preference for transcriptionally active regions was thus inverted in a dose dependent manner upon treatment with LEDGINs (CX014442).

4

LEDGIN Treatment Increases the Silent Latent Virus Reservoir

Figure 3:
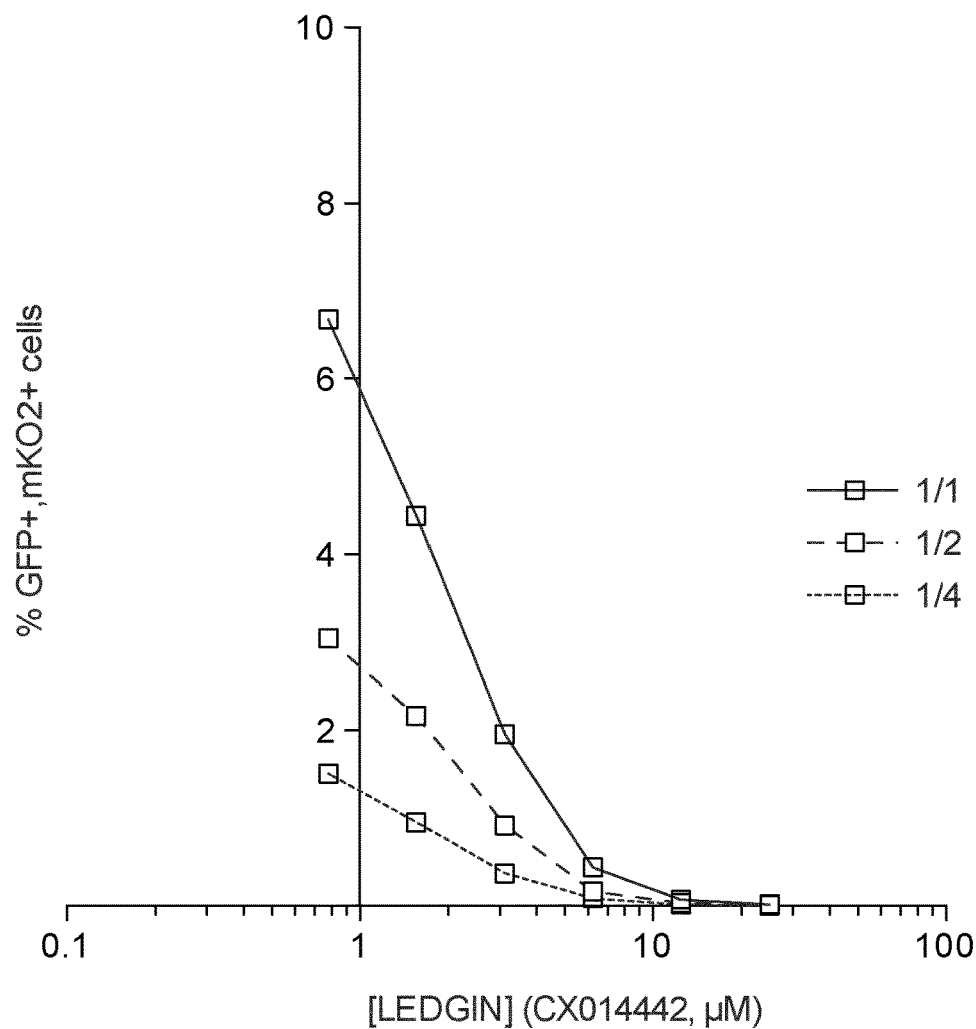
FIG. 3: LEDGIN mediated retargeting of integration increases the fraction of silently infected cells. SupT1 cells were infected with three different dilutions of HIV OGH. (A) Dose-response curve showing a decrease in productively infected cells (% eGFP+, mKO2+ cells) with increasing LEDGIN concentration. Three different virus concentrations are depicted. (B) Dose-response curve showing a decrease in the overall % mKO2 positive cells with increasing LEDGIN concentration. Three different virus concentrations are depicted. (C) The fraction of quiescent cells (% eGFP−, mKO2+ cells)/(% mKO2+ cells)*100 or silently infected cell population increases upon addition of LEDGINs. Three different vector dilutions are depicted. All viruses are VSV-G pseudotyped. GFP, Enhanced Green Fluorescent Protein; mKO2, Mutant Kusubira Orange 2.
Figure 3:
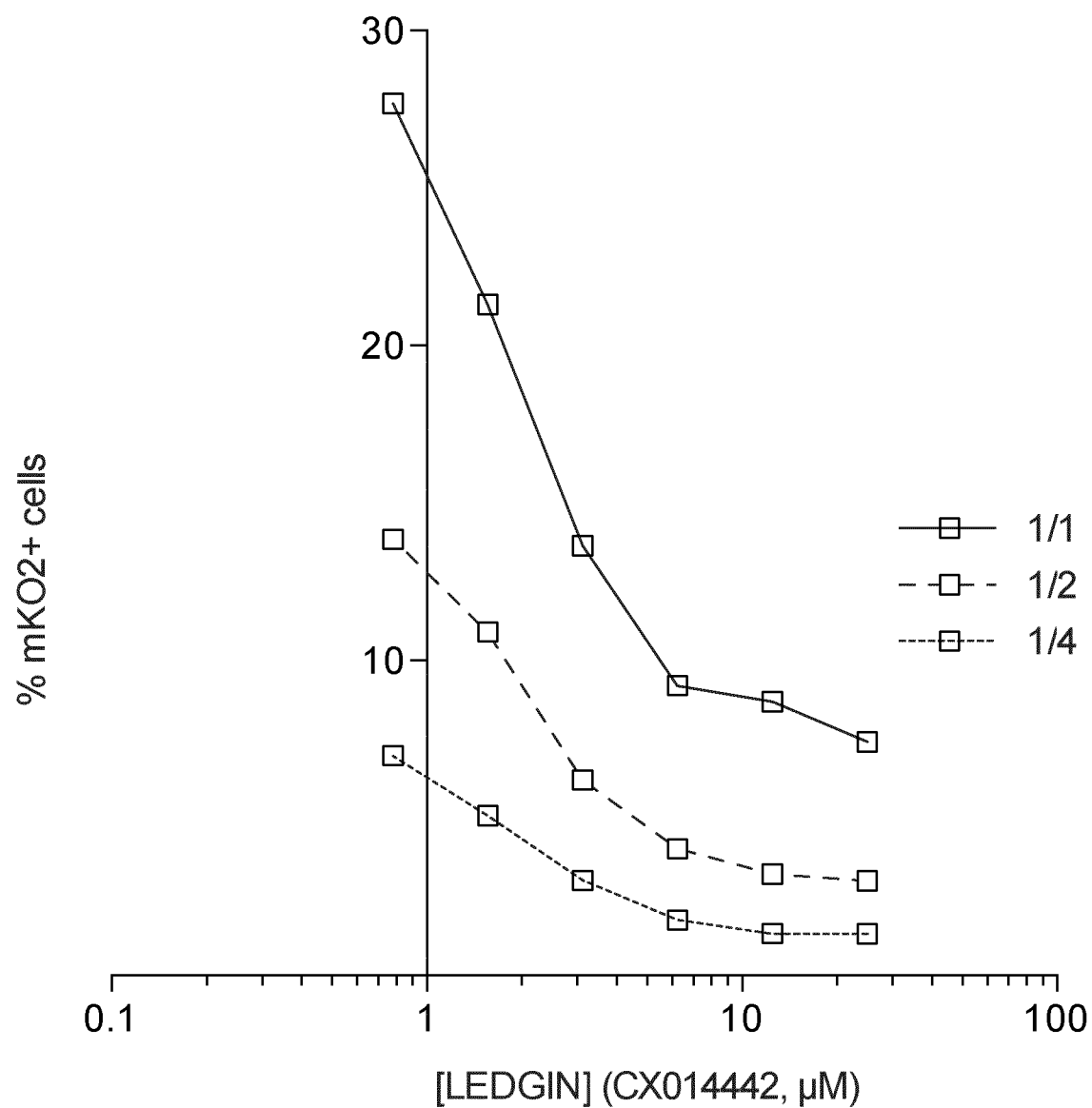
Figure 3:
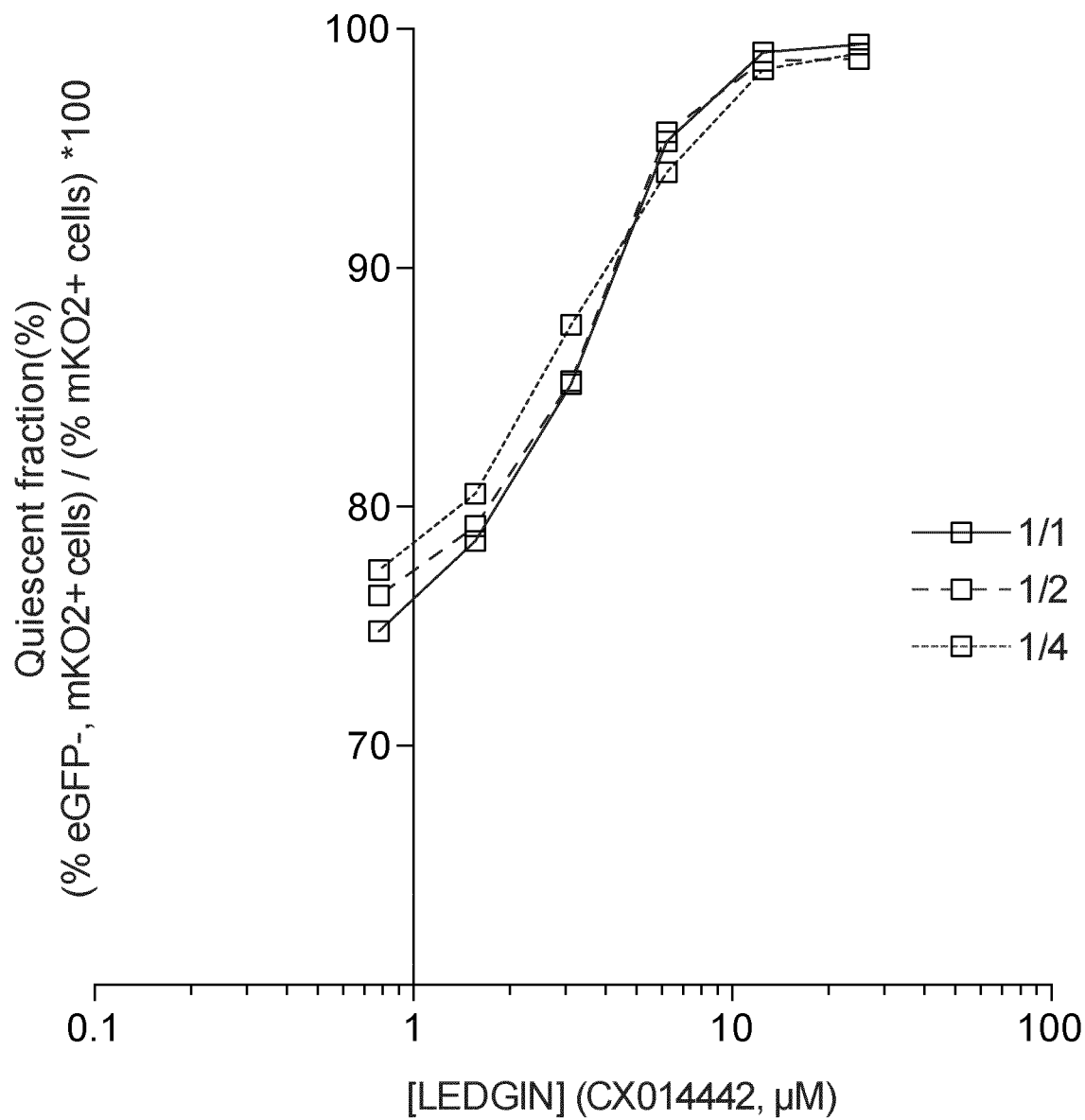

It was further investigated whether LEDGIN mediated retargeting also affects the latent reservoir, as demonstrated earlier for LEDGF/p75 KD/KO cells. SupT1 cells were infected with the VSV-G pseudo-typed double reporter virus HIV OGH in the presence of increasing concentrations of LEDGIN (CX014442) able to disrupt the LEDGF/p75-IN interaction and retarget lentiviral integration outside the body of genes. HIV OGH infection was measured 3 days post infection using flow cytometry resulting in the detection of both productive (eGFP+/mKO2+) and latent (eGFP−/mKO2+) cell populations (see also FIG. 1B). LEDGIN treatment induced a dose dependent decrease in % eGFP$^+$, mKO2$^+$ cells (FIG. 3A) as well as the overall % mKO2 positive cells (FIG. 3B). However, similar to LEDGF/p75 depletion (FIG. 1C), LEDGIN addition resulted in an increase in the fraction of latently infected (% eGFP$^−$,

TABLE 1

Integration frequency near mapped genomic features in the human genome. The percentage of HIV-based vector integration sites relative to features specific for integration such as integration into the body of genes (Refseq genes), TSS, CpG islands and DNase I-hypersensitive sites is shown. 2 kb and 4 kb windows are shown. Data are obtained from SupT1 cells. Asterisks depict a significant deviation from the DMSO treated control dataset (two-tailed Chi-square test; ***, p-values < 0.001). TSS, Transcription start sites; DHS, DNase I-hypersensitive sites.

| Compound concentration (µM) | Total sites | % in RefGene | % TSS within 2 kb | % TSS within 4 kb | % CpG within 2 kb | % CpG within 4 kb | % DHS within 2 kb | % DHS within 4 kb |
|---|---|---|---|---|---|---|---|---|
| DMSO (control) | 3312 | 69.54 | 1.78 | 5.62 | 2.02 | 6.16 | 23.04 | 39.86 |
| 0.54 | 2451 | 70.58 | 2.00 | 5.92 | 2.33 | 5.83 | 24.07 | 39.94 |
| 1.5 | 2278 | 70.37 | 2.41 | 5.88 | 2.37 | 5.79 | 20.94 | 37.18 |
| 3 | 2485 | 66.60 | 1.97 | 5.59 | 1.73 | 5.39 | 21.49 | 37.55 |
| 6 | 3364 | 65.23** | 3.03 | 6.45 | 2.97 | 6.39 | 21.78 | 37.12 |
| 12 | 884 | 61.88*** | 3.96** | 7.58 | 3.39 | 7.35 | 23.6 | 38.57 |
| 25 | 604 | 60.93*** | 4.30** | 8.94 | 4.97** | 10.26** | 22.19 | 40.07 |
| 50 | 418 | 54.55*** | 6.94*** | 12.68*** | 5.50** | 11.72*** | 26.08 | 40.67 |

Figure 4:
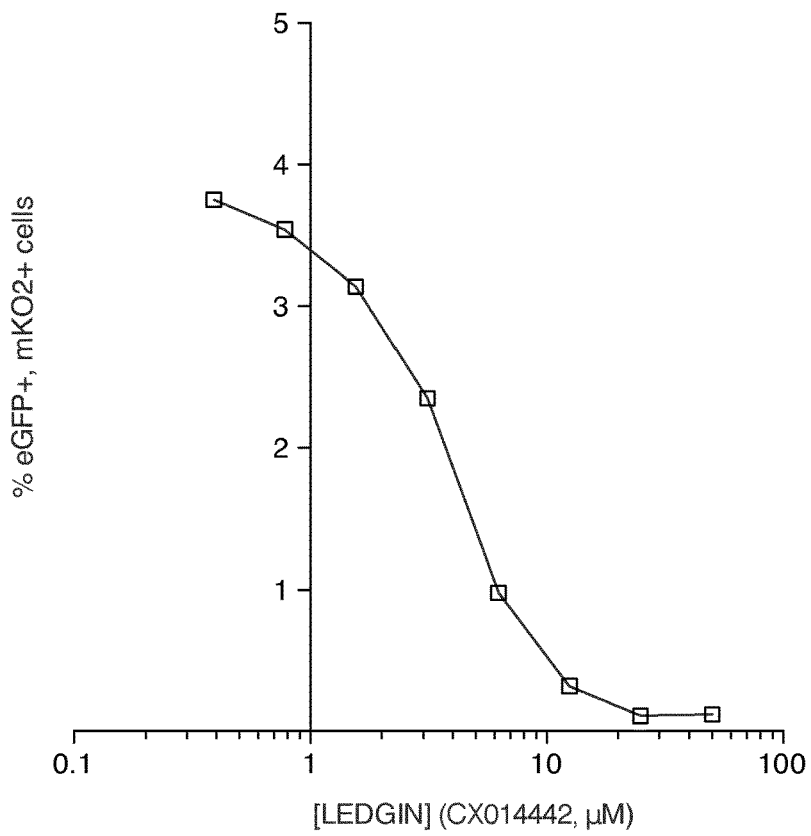
FIG. 4: LEDGIN mediated inhibition of lentiviral transduction. Activated CD4+ T-cells were infected with single round double reporter virus (OGH) and the % eGFP− % mKO2 positive cells were monitored. (A) Dose-response curve showing a decrease in % eGFP+, mKO2+ cells with increasing LEDGIN concentration. (B) The fraction of silently infected cell population (% eGFP−, mKO2+ cells)/(% mKO2+ cells)*100 increases upon addition of LEDGINs. All vectors are VSV-G pseudotyped. GFP, Enhanced Green Fluorescent Protein.
Figure 4:
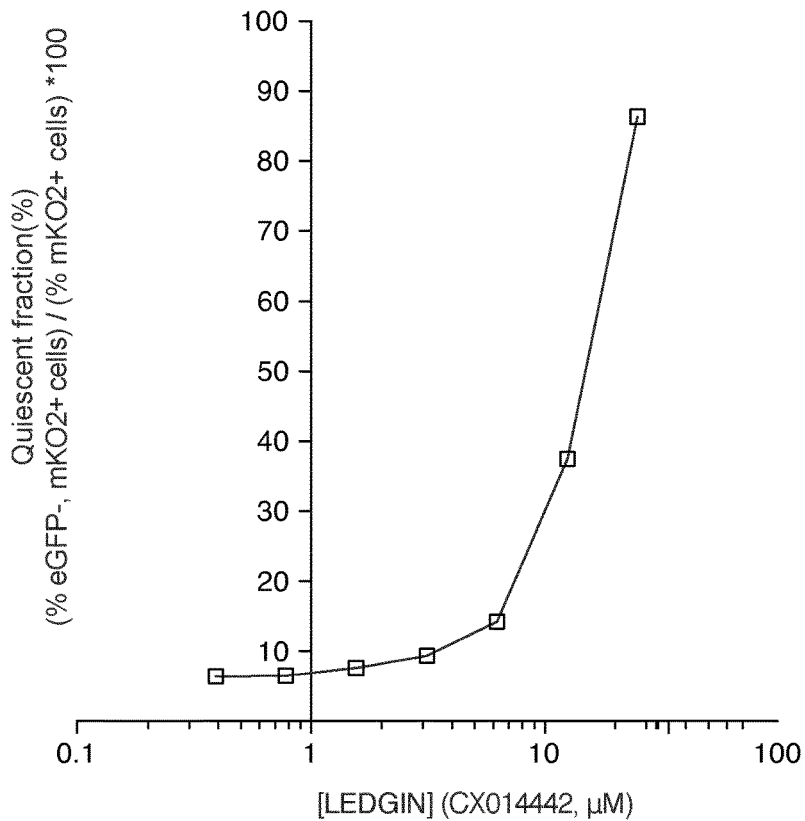

In a more elaborate analysis we included a wide selection of genomic features and compared integration site data sets to those obtained from SupT1 LEDGF/p75 wt (DMSO treated) cells. When analysing global integration preferences, LV integration upon LEDGF/p75 KD shifted integration out of transcriptionally active regions. This shift in correlation was also observed under LEDGINs treatment where a significant difference compared to wt was reached at concentrations above 12 µM. Additionally we analyzed integration site densities relative to epigenetic features described in T-cells (data not shown). Lentiviral integration correlated with histone marks associated with transcriptionally active chromatin (H3K4 mono-, di- and tri methylation, H3K14 and H4 acetylation, as well as acetylation and monomethylation of H3K9/K27/K79, H4K20 and H2BK5).

mKO2$^+$ cells)/(% mKO2$^+$ cells)*100 cells (FIG. 3C). 100% latently infected cells were obtained at a LEDGIN (CX014442) concentration of 25 µM. Next the role of the LEDGF/p75-IN interplay in activated primary CD4+ T-cells was investigated. Peripheral Blood Mononuclear cells (PBMCs) were purified and CD4+ T-cells selectively enriched using Bi-specific MAb CD3.8 (AIDS reagents) for 5 days and infected with the OGH reporter virus. HIV infection was monitored 3 days post infection using flow cytometry analysis (FIG. 4). Similar to the results observed in SupT1 cells, the % latently infected cells increased upon addition of LEDGINs (CX014442) during infection. The lower percentage of latently infected cells in the absence of LEDGIN can be explained by the selective enrichment of CD4+ T-cells and a lower activity of the EF1α promoter in primary cells.

LEDGIN Treatment Reduces HIV Reactivation from Latency

Figure 5:
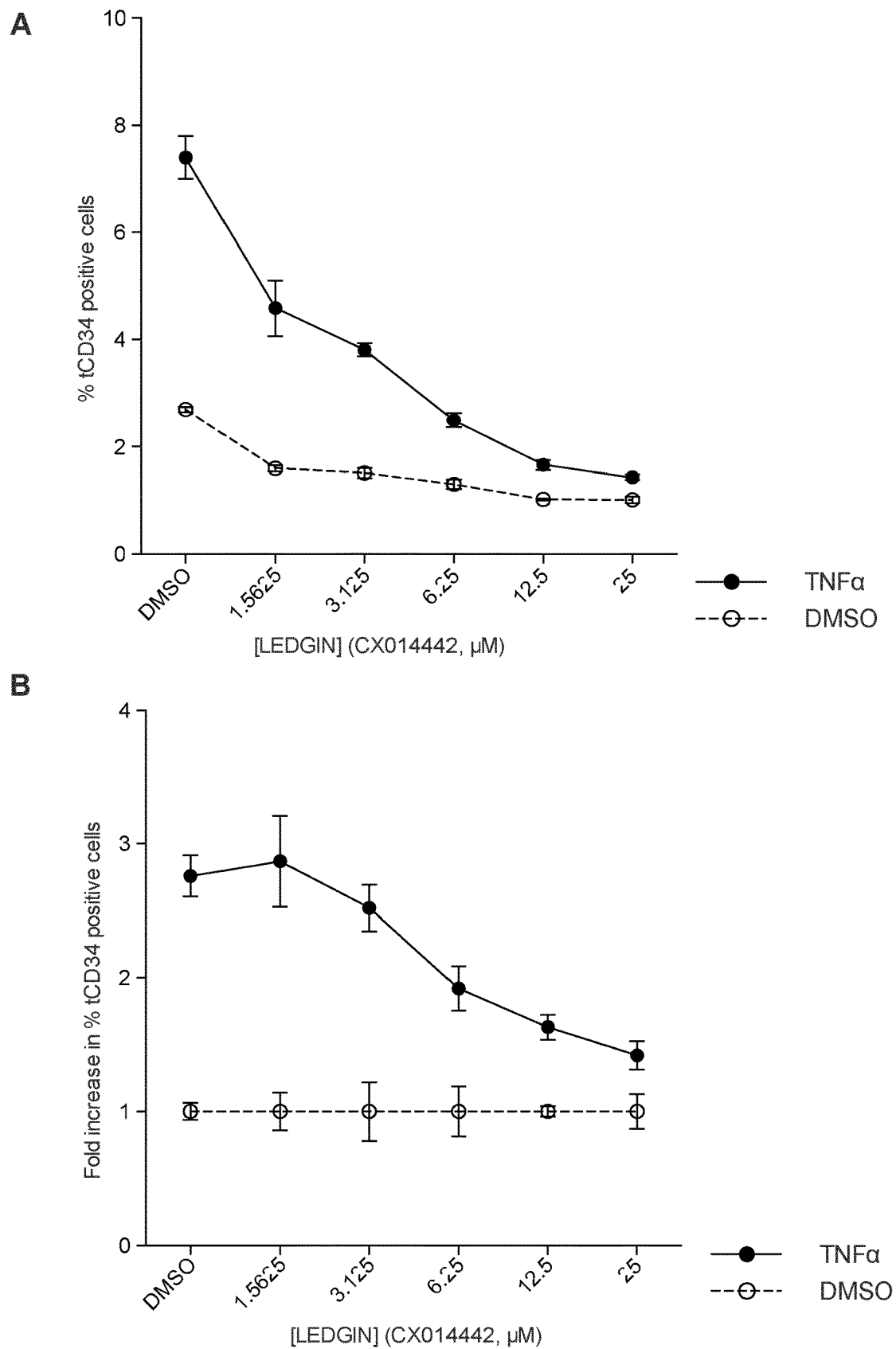
FIG. 5: LEDGIN treatment reduces reactivation from latency. SupT1 cells were infected with single round reporter virus NL4.3 tCD34 and treated with different concentrations of CX14442 as indicated and the % tCD34 positive cells were monitored. 11 days post infection cells were reactivated using TNFalpha (10 ng/mL). (A) The % tCD34 positive cells after stimulation with TNFalpha or DMSO is depicted. (B) The fold increase in % tCD34 cells relative to DMSO treatment is depicted. (C) The % tCD34 positive cells*the MFI observed after stimulation with TNFalpha or DMSO is depicted. (D) The fold increase in % tCD34*the MFI observed relative to DMSO treatment is depicted. All data represent averages of 3 replicates and error bars indicate the standard deviation. All viruses are VSV-G pseudotyped. tCD34; truncated Cluster of Differentiation 34, DMSO; Dimethyl Sulfoxide, TNFalpha; Tumor Necrosis Factor alpha.
Figure 5:
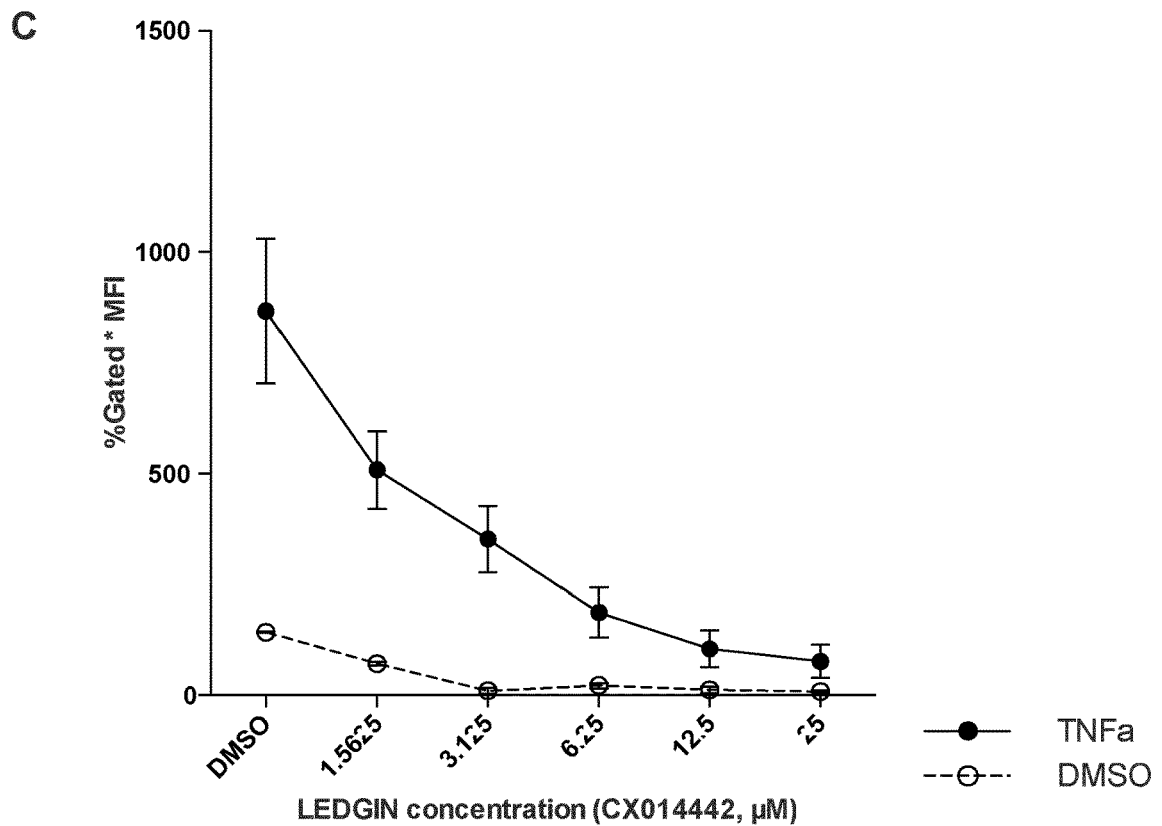
Figure 5:
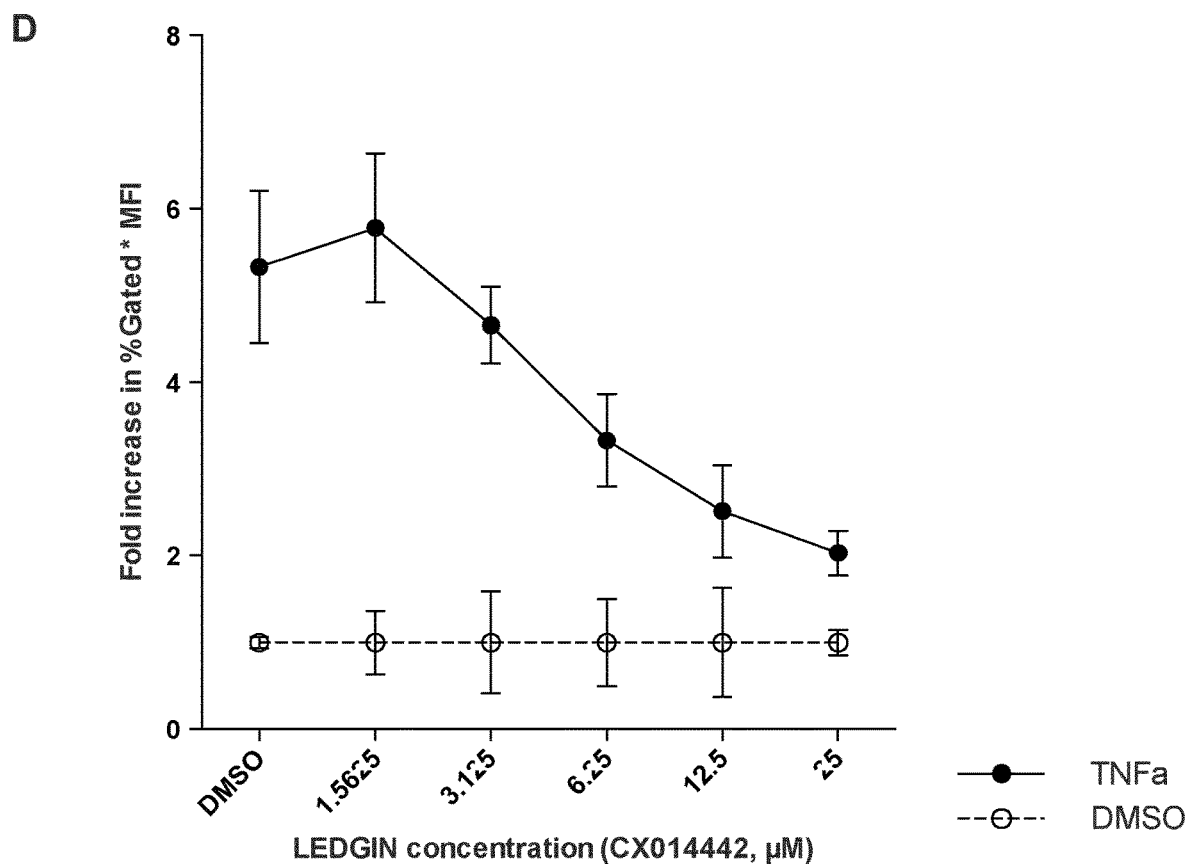

Next it was determined whether LEDGIN treatment also reduced reactivation after reporter gene silencing as observed after LEDGF/p75 depletion (FIG. 2B). The LEDGIN-induced increase in the latent reservoir together with a reduction in HIV reactivation potential implies the possibility of a functional cure of HIV/AIDS. SupT1 cells were infected with single round HIV NL4-3.tCD34.R-.E- (VSVG, FIG. 2A), at a MOI yielding <30% positive cells and treated with 3-25 µM LEDGIN CX014442. The infected cells were cultured for two weeks in order for silencing to occur. In a first experiment cells were stimulated 11 days post infection using TNFalpha (10 ng/mL) for 24 hrs, in order to obtain a maximal T-cell activation response. LEDGIN (CX014442) treatment resulted in a dose dependent inhibition of reactivation from latency (EC50=7.24 µM) as evidenced by the reduced increase in % tCD34 positive cells and the reduced increase in mean fluorescence intensity (MFI) multiplied by the % tCD34 positive cells (FIG. 5). Similar results were obtained when stimulating the latent proviral pool using other LRAs (data not shown).

Figure 2:
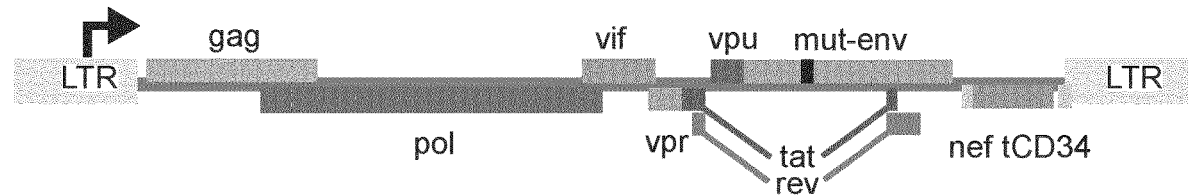
FIG. 2: LEDGF/p75 depletion reduces reactivation from latency. (A) Schematic representation of the single round HIV reporter virus encoding a tCD34 driven by the viral LTR promoter in the nef position. (B) Bar diagram depicting the fold reactivation (as fold increase in % tCD34 positive cells). Nalm wt (+/c) and Nalm LEDGF/p75 KO (−/−) cells were infected with a dilution series of single round reporter virus and the % tCD34 positive cells was monitored. 11 days post infection cells were reactivated using different LRAs at concentrations indicated. Data represent averages of 9 replicates and error bars indicate the standard deviation. A statistical analysis was performed using multiple t tests and corrected using Sidak-Bonferroni (*p<0.05, **p<0.005 vs. LEDGF/p75 KO) (SAHA; Suberoylanilide Hydroxamic Acid, TNFalpha; Tumor Necrosis Factor alpha, PMA; Phorbol 12-Myristate 13-Acetate, Prostratin, DMSO; Dimethyl sulfoxide.). Normalization was based on equal integrated copy numbers. All viruses are VSV-G pseudotyped. tCD34; truncated Cluster of Differentiation 34.
Figure 2:
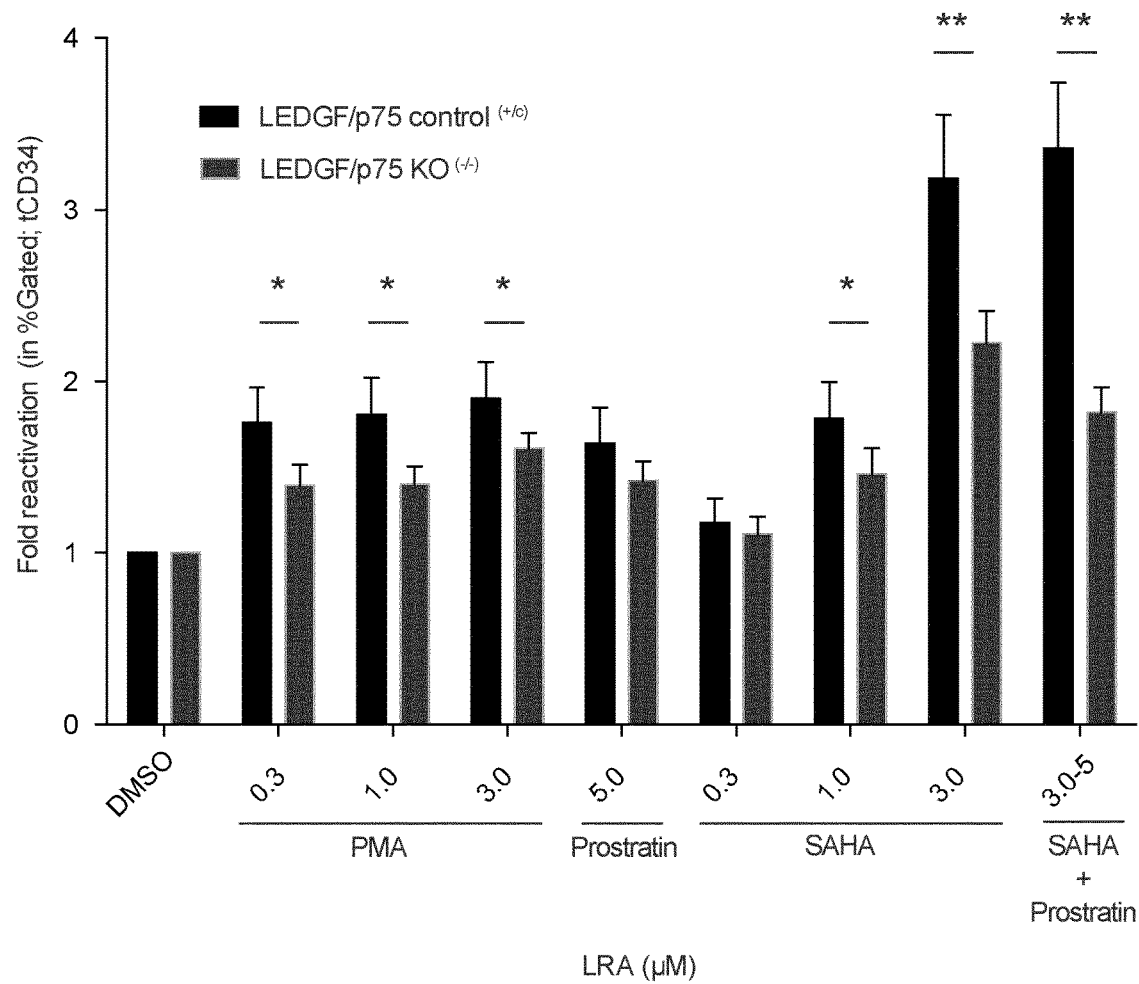
Figure 6:
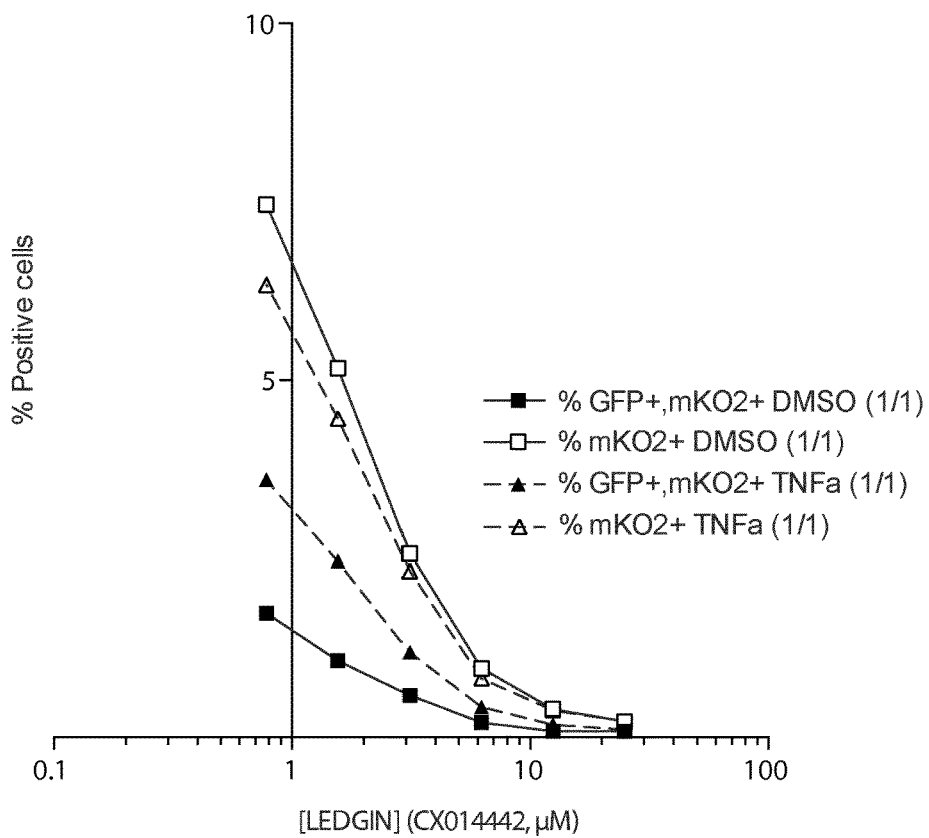
FIG. 6: LEDGIN treatment reduces reactivation from latency. SupT1 cells were infected with a dilution series of single round double reporter virus (OGH) and the % eGFP− % mKO2 positive cells were monitored. 11 days post infection cells were reactivated using TNFalpha (10 ng/mL). (A, B) Dose-response curve showing the % eGFP+, mKO2+ cells and overall % mKO2 positive cells after reactivation with DMSO or TNFalpha. Two different virus concentrations are depicted panel A and B. (C) Average fold increase in percentage eGFP+, mKO2+ or productively infected cells after stimulation with TNF alpha relative to the DMSO treated condition. (D) Average decrease in the fraction quiescent cells (% eGFP−, mKO2+ cells)/(% mKO2+ cells)*100 or silent reservoir fraction upon stimulation with TNF alpha relative to the DMSO treated condition. Data in panels C and D represent averages of 3 different vector dilutions and error bars indicate the standard deviation. All viruses are VSV-G pseudotyped. GFP, Enhanced Green Fluorescent Protein; mKO2, Mutant Kusubira Orange 2, TNFalpha; Tumor Necrosis Factor alpha, DMSO; Dimethyl sulfoxide.
Figure 6:
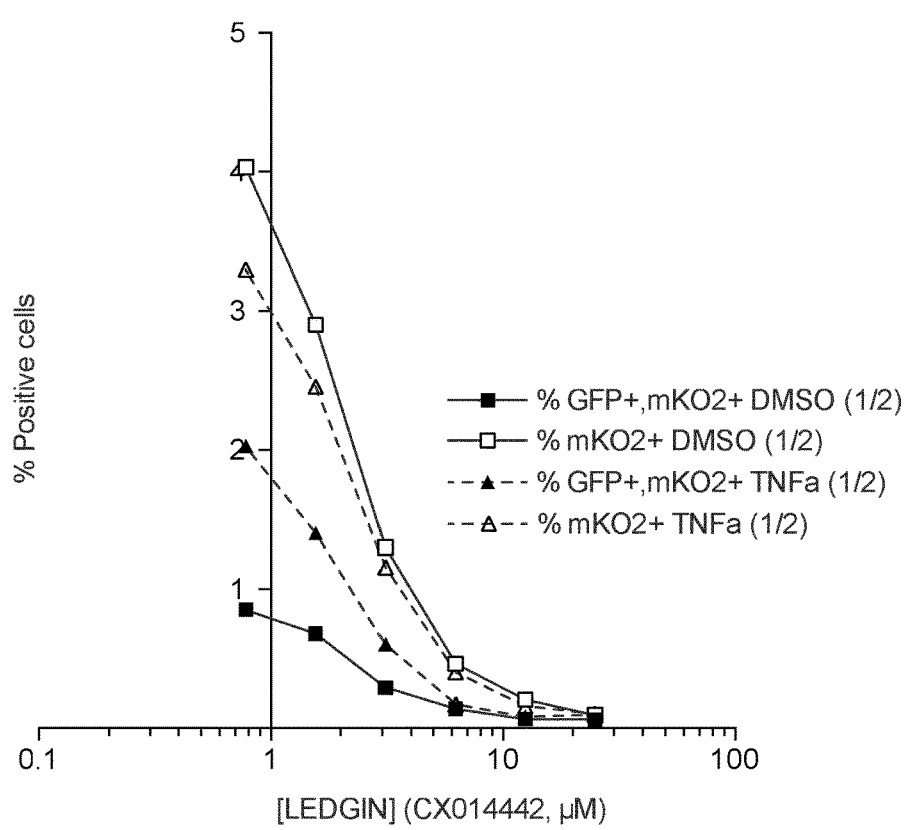
Figure 6:
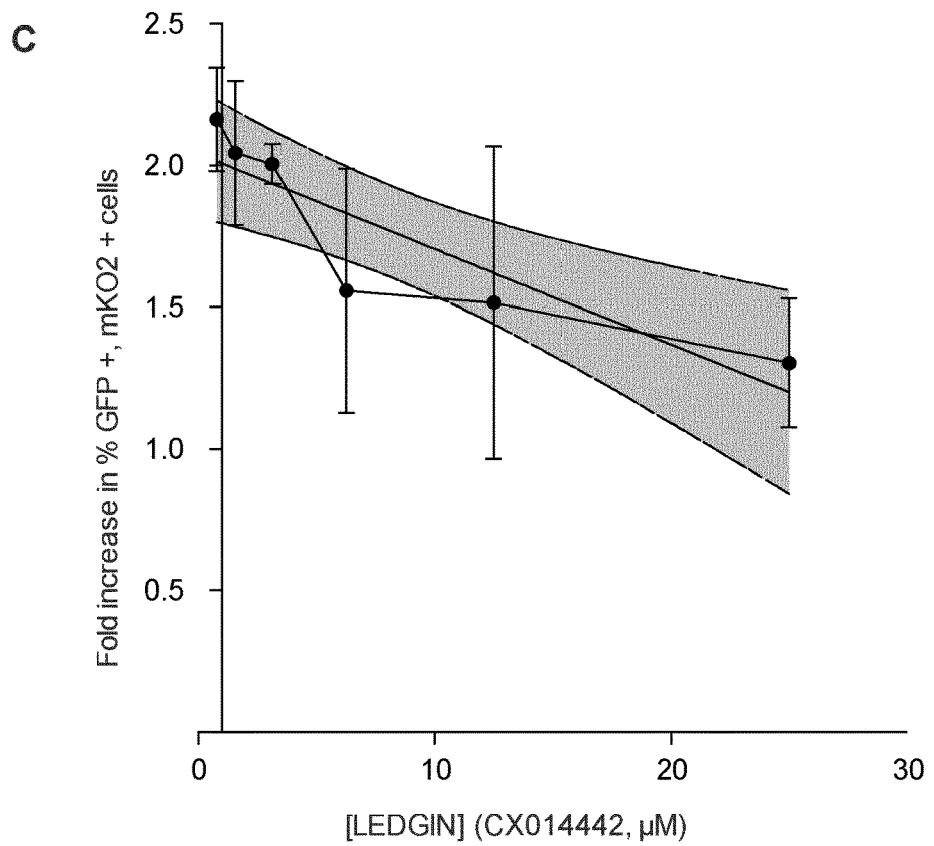
Figure 6:
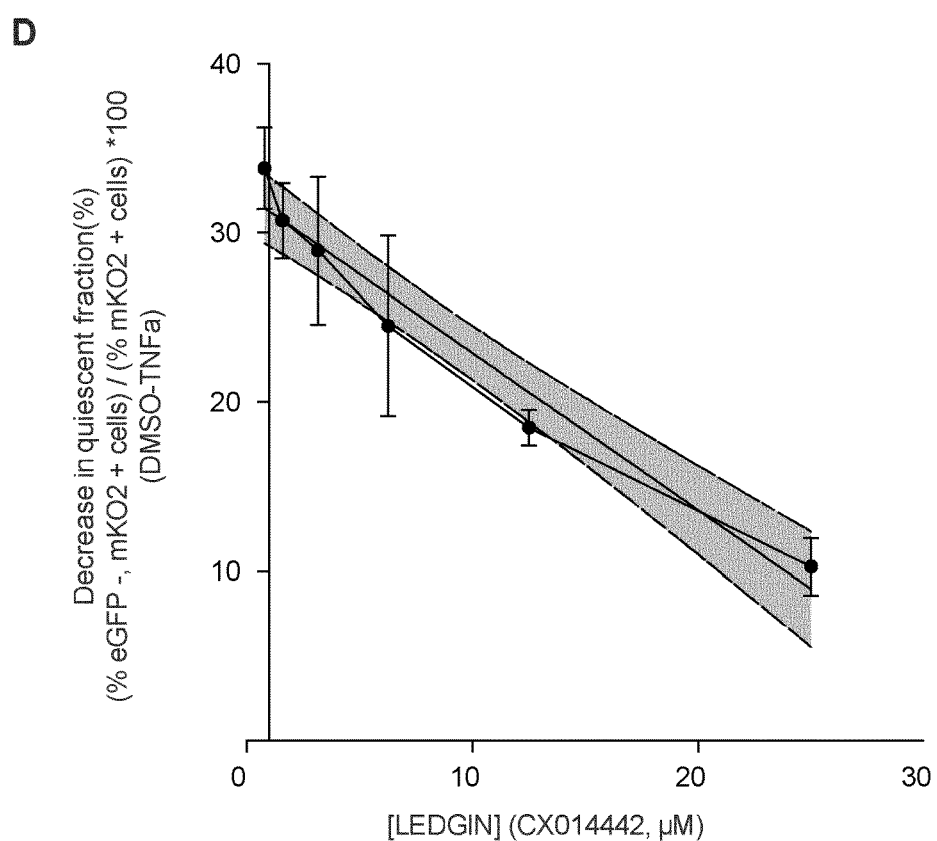

To corroborate these findings SupT1 cells were infected with the HIV-OGH double reporter virus under different LEDGIN (CX014442) concentrations. SupT1 cells were infected and reactivated under conditions similar to the experiment with HIV tCD34 (FIGS. 2 and 5). Data are represented in FIG. 6. Two different virus dilutions are depicted in panel A and B. In both graphs the percentage eGFP+, mKO2+ cells and overall % mKO2 positive cells is plotted after stimulation with DMSO or TNFα for 24 h. The dashed lines show an increase in percentage of eGFP+, mKO2+ cells after stimulation with TNFα0 compared to DMSO, while the overall percentage of mKO2 positive cells remains constant. LEDGIN treatment reduces the reactivation of eGFP+, mKO2+ cells in a concentration-dependent manner, with 50 µM of CX014442 reducing reactivation to only 1.5-2 fold (FIG. 6C). Likewise increasing concentrations of LEDGIN CX014442 counteracted the decrease in the latent HIV-1 pool represented by (% eGFP−, mKO2+ cells)/(% mKO2+ cells)*100 (FIG. 6D).

LEDGIN Treatment Retargets HIV Integration into Safer Locations

Figure 8:
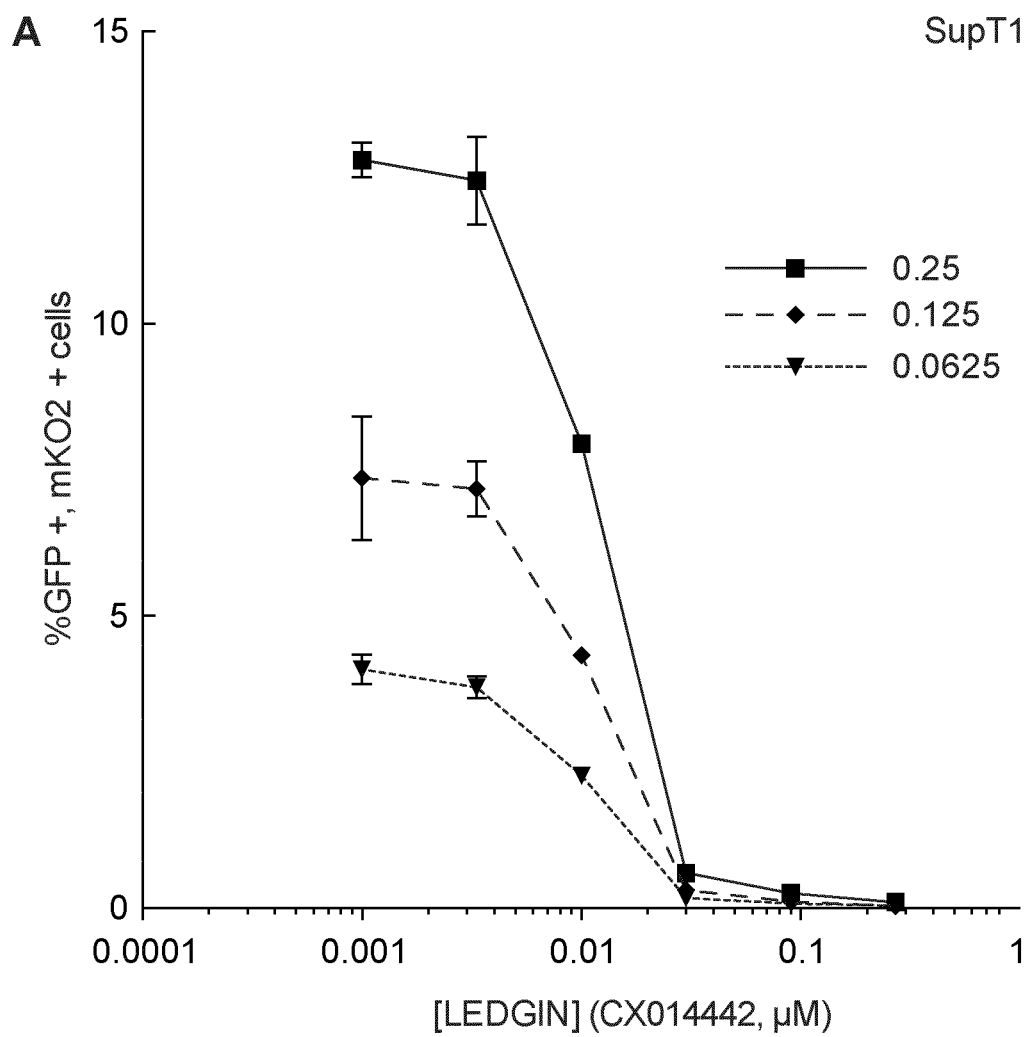
FIG. 8. Addition of LEDGINs during production results in transcriptionally silent provirus after integration. HIV-1 double reporter virus (OGH) was produced in HEK293T cells in the presence of varying LEDGIN concentrations. Infection of either SupT1 cells (A, C, E) or THP1 cells (B, D, F) with HIV-1 double reporter virus produced in the presence of increasing concentrations of LEDGIN CX014442 ('late' IC50=0.06 µM). (A, B) Dose-response curves showing a decrease in % eGFP+, mKO2+ cells with increasing LEDGIN concentration. Three different virus concentrations are depicted in the graphs. (C, D) Dose-response curves showing a decrease in the overall % mKO2+ cells with increasing LEDGIN concentration. Three different virus concentrations are depicted in the graphs. (E, F) The fraction of quiescent cells (% eGFP−, mKO2+ cells)/(% mKO2+ cells)*100 increased proportionally with the concentration of LEDGIN added during production. Three different virus concentrations used are shown in the graphs. All viruses were VSV-G pseudotyped. eGFP, Enhanced Green Fluorescent Protein; mKO2, Mutant Kusubira Orange 2.
Figure 8:
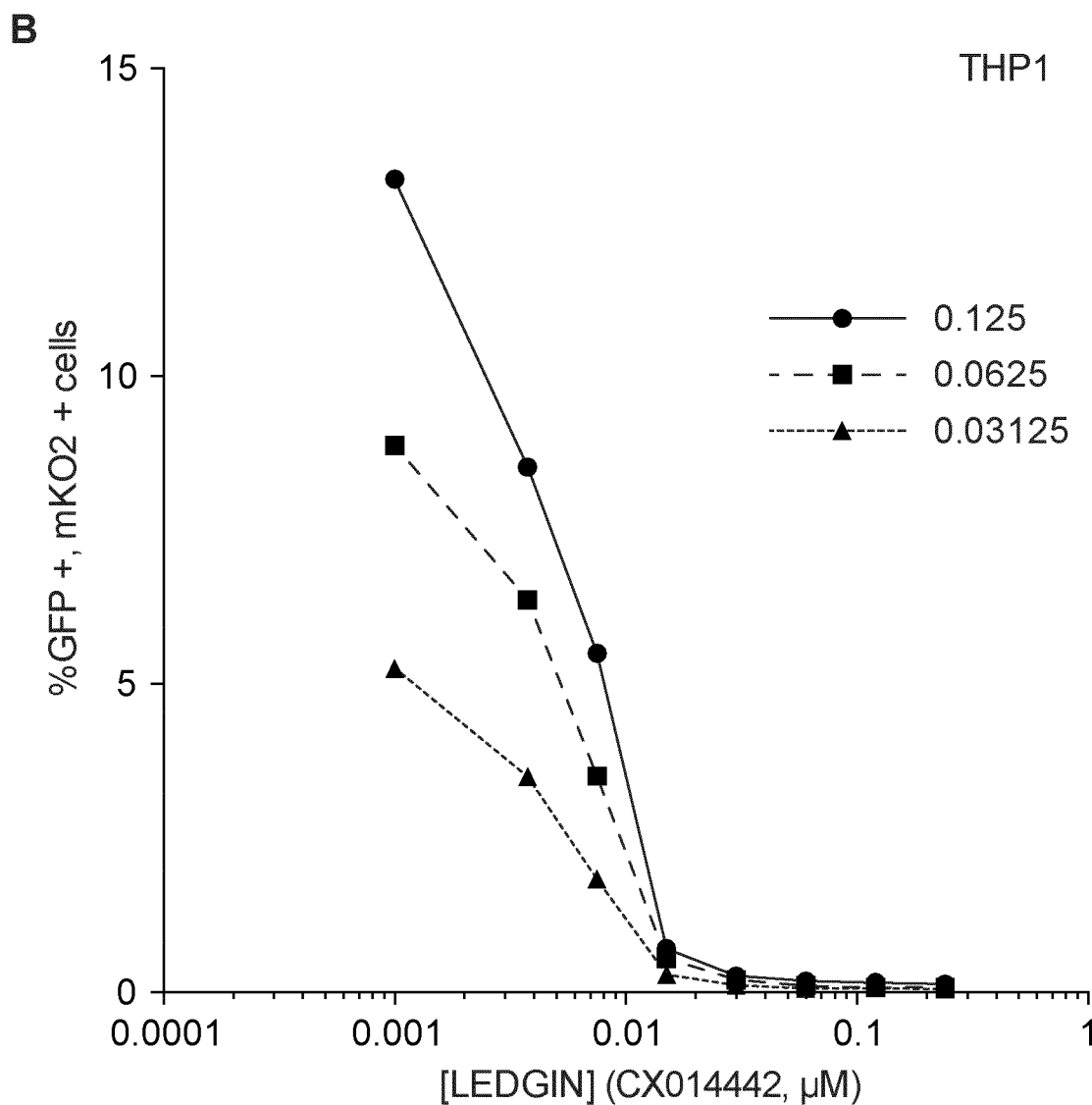
Figure 8:
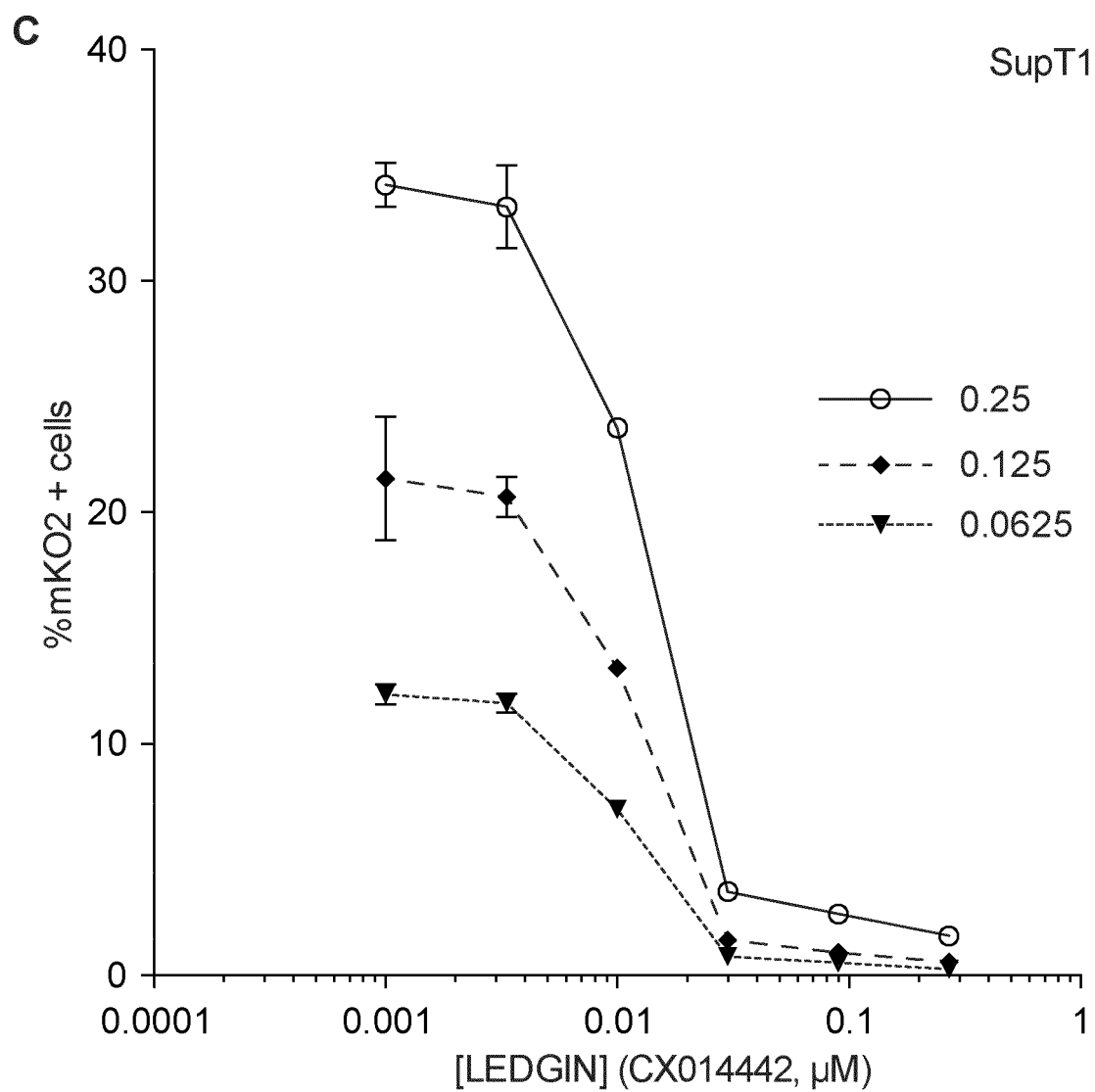
Figure 8:
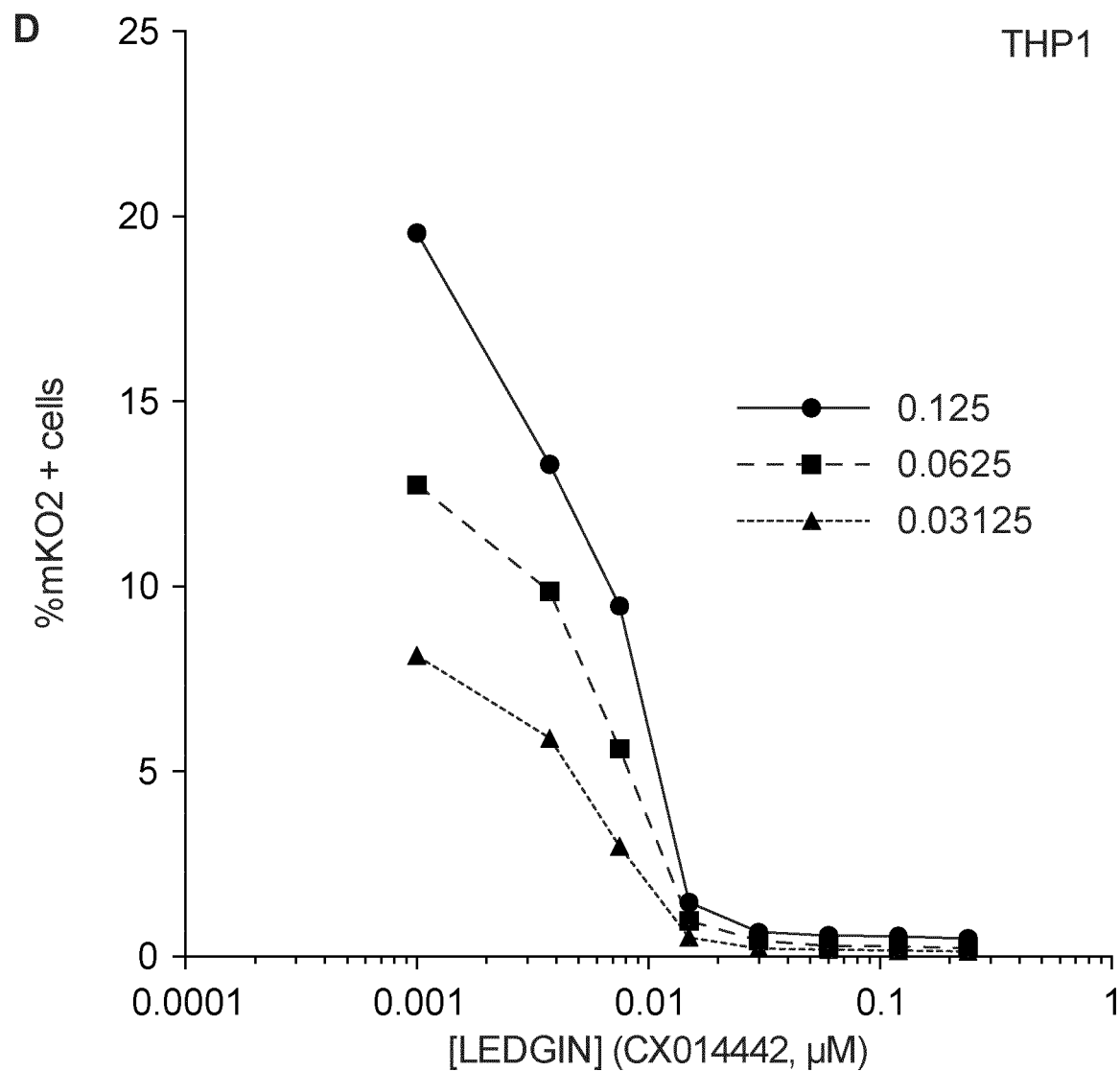
Figure 8:
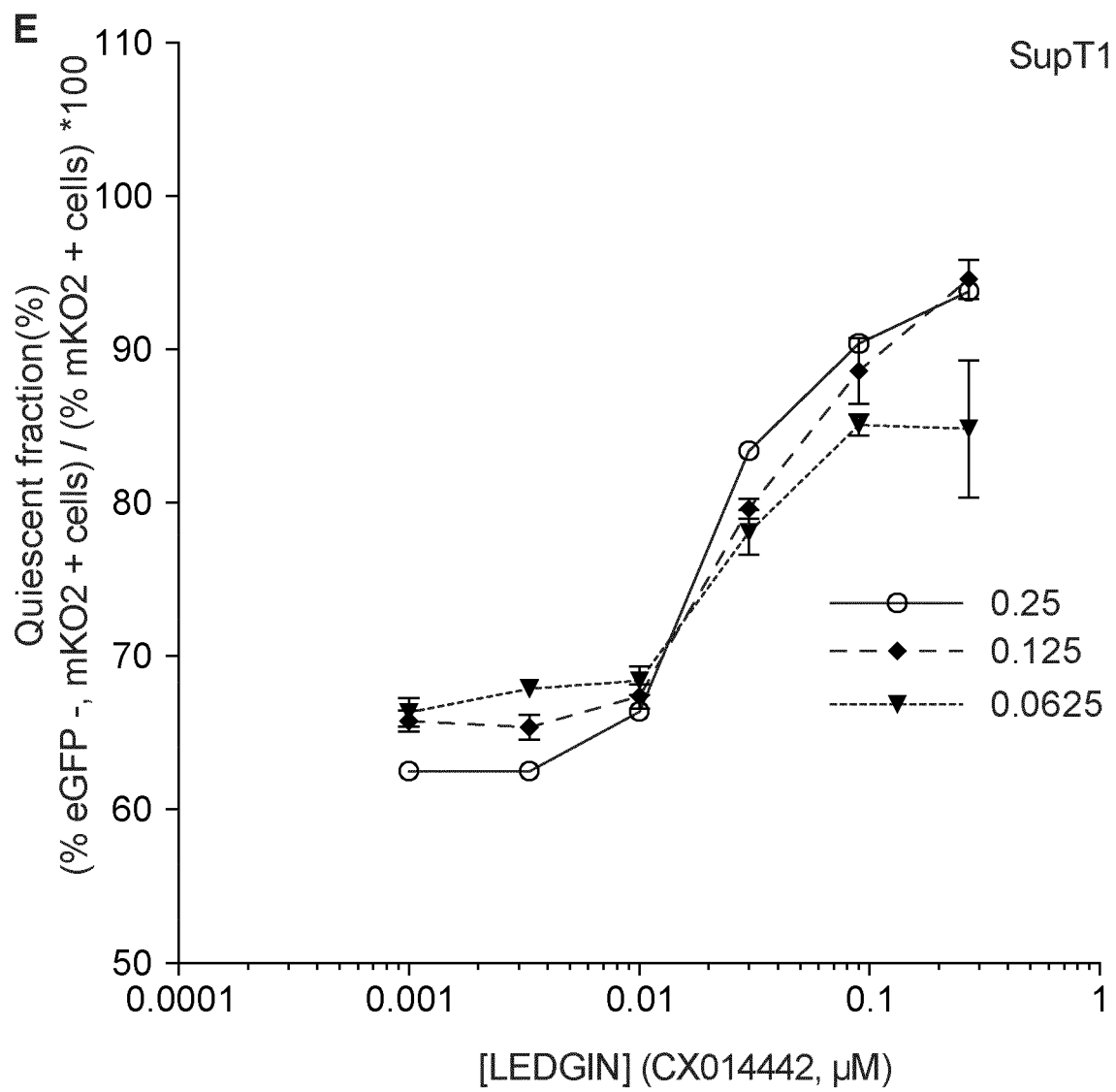
Figure 8:
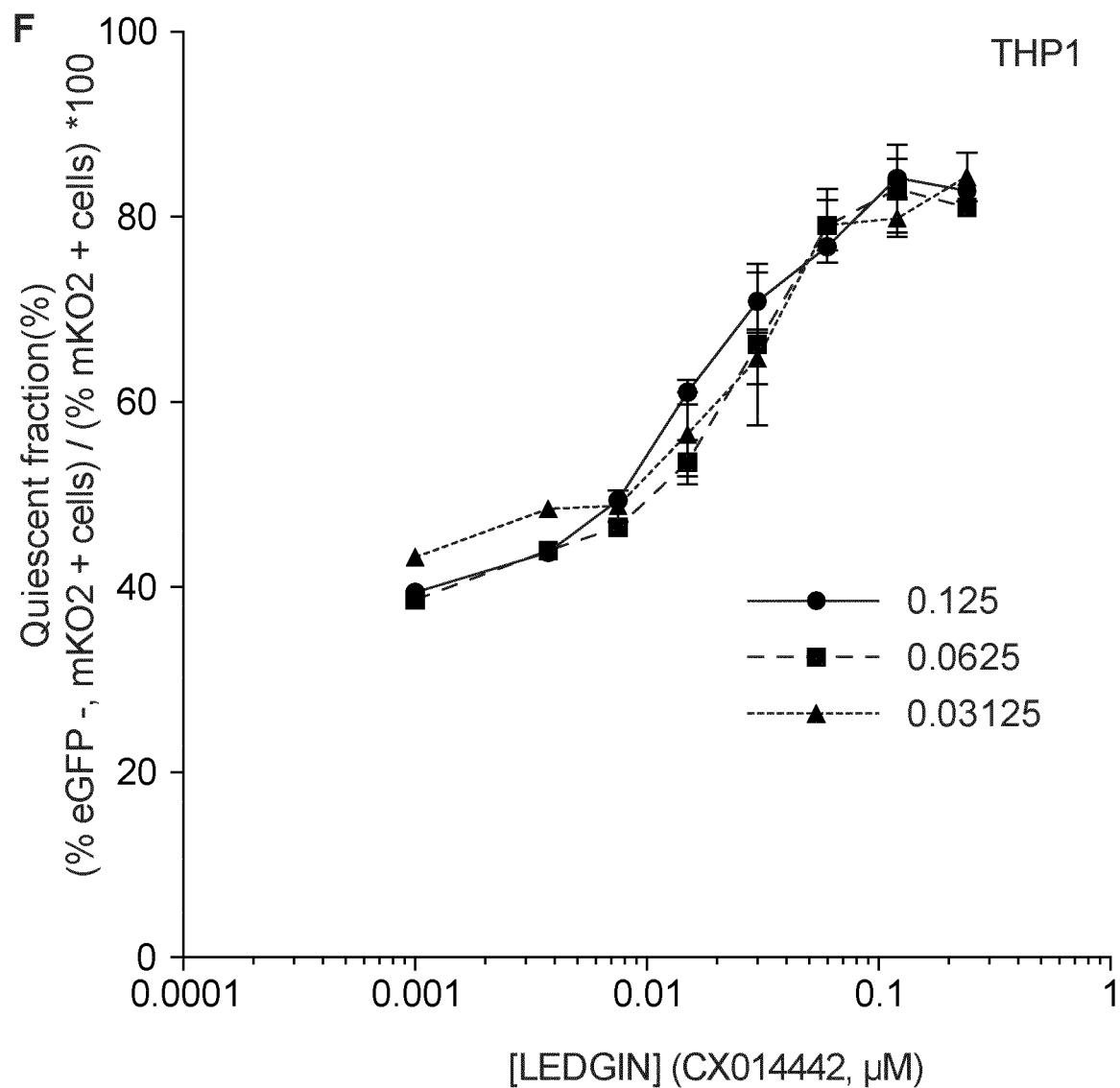

Recently, two studies revealed the existence of clonally expanded CD4+ cell populations in HIV-1 patients on prolonged antiretroviral therapy. The strategy to enhance the quiescent HIV reservoir by retargeting integration into silent chromatin is associated with the theoretical risk for increased insertional mutagenesis. Therefore the "safety" of the integration pattern obtained under LEDGIN treatment was investigated. The following criteria that define potentially unsafe integration events were considered: integration near transcription start sites (<50 kb), oncogenes (<300 kb) or miRNA coding regions (<300 kb), and integration into transcription units and ultra-conserved elements. Sites outside of all of these features are considered to be safe (Papapetrou et al., 2011). For each data set, we evaluated the percentage of potentially unsafe integration sites according to a given criterion (Table 2) and determined the final percentage of safe sites (not falling into any of these regions). In the parental SupT1 cell line only 10.7% of all vector integration sites are considered safe. LEDGF/p75 depletion increases the percentage safe sites to 14.7% (a phenotype that is reverted upon LEDGF/p75 BC complementation, data not shown). Since our data indicate a shift in integration site distribution under LEDGIN treatment, resembling the effect of LEDGF/p75 depletion, the dose-dependent increase in percentage of safe integrations (16.51% at 50 µM) does not come as a surprise. Apart from increasing the latent reservoir and decreasing the likelihood of HIV reactivation, LEDGIN treatment may thus be associated with a reduced risk of clonal expansion due to insertional mutagenesis in HIV-infected patients, therefore inducing a safer and silent latent reservoir. Interestingly, in more recent experiments the addition of submicromolar concentrations of LEDGINs during virus production results in virus particles that after integration are again refractory to LTR-driven gene expression (FIG. 8), suggesting that during multiple round replication also low concentrations of LEDGINs induce quiescent proviral pools.

TABLE 2

Integration frequency near safe harbor criteria. Table showing the percentage of HIV-based vector integration sites relative to features used to define UNsafe harbors. These criteria are considered to be UNsafe: TSS, Oncogenes, miRNA encoding regions, Transcription units and ultra-conserved regions. The % integrations negatively associated with these 5 features is used to calculate a safety profile. TSS, Transcription start sites; UCR, Ultra conserved regions.

| Compound concentration (µM) | total sites | % within 50 kb of TSS | % within 300 kb of onco | % within 300 kb of miRNAs | % in transcript. Units | % in UCR | Total % safe |
|---|---|---|---|---|---|---|---|
| DMSO (control) | 3312 | 32.04 | 31.71 | 25.88 | 74.68 | 7.29 | 10.24 |
| 0.78125 | 2451 | 31.13 | 38.15 | 25.54 | 74.95 | 6.36 | 11.14 |
| 1.5625 | 2278 | 29.28 | 35.47 | 22.52 | 75.11 | 7.24 | 10.36 |
| 3.125 | 2485 | 28.57 | 35.45 | 23.34 | 71.91 | 7.77 | 11.31 |
| 6.25 | 3364 | 29.46 | 33.03 | 21.76 | 70.48 | 6.03 | 13.32 |
| 12.5 | 884 | 31.33 | 33.03 | 24.89 | 67.42 | 9.39 | 13.24 |
| 25 | 604 | 29.80 | 35.26 | 21.52 | 66.06 | 6.95 | 14.57 |
| 50 | 418 | 32.54 | 35.65 | 22.25 | 59.57 | 5.98 | 16.51 |
| LEDGF/p75 KD | 4664 | 32.22 | 36.16 | 21.67 | 64.96 | 6.72 | 14.71 |

7

Figure 7:
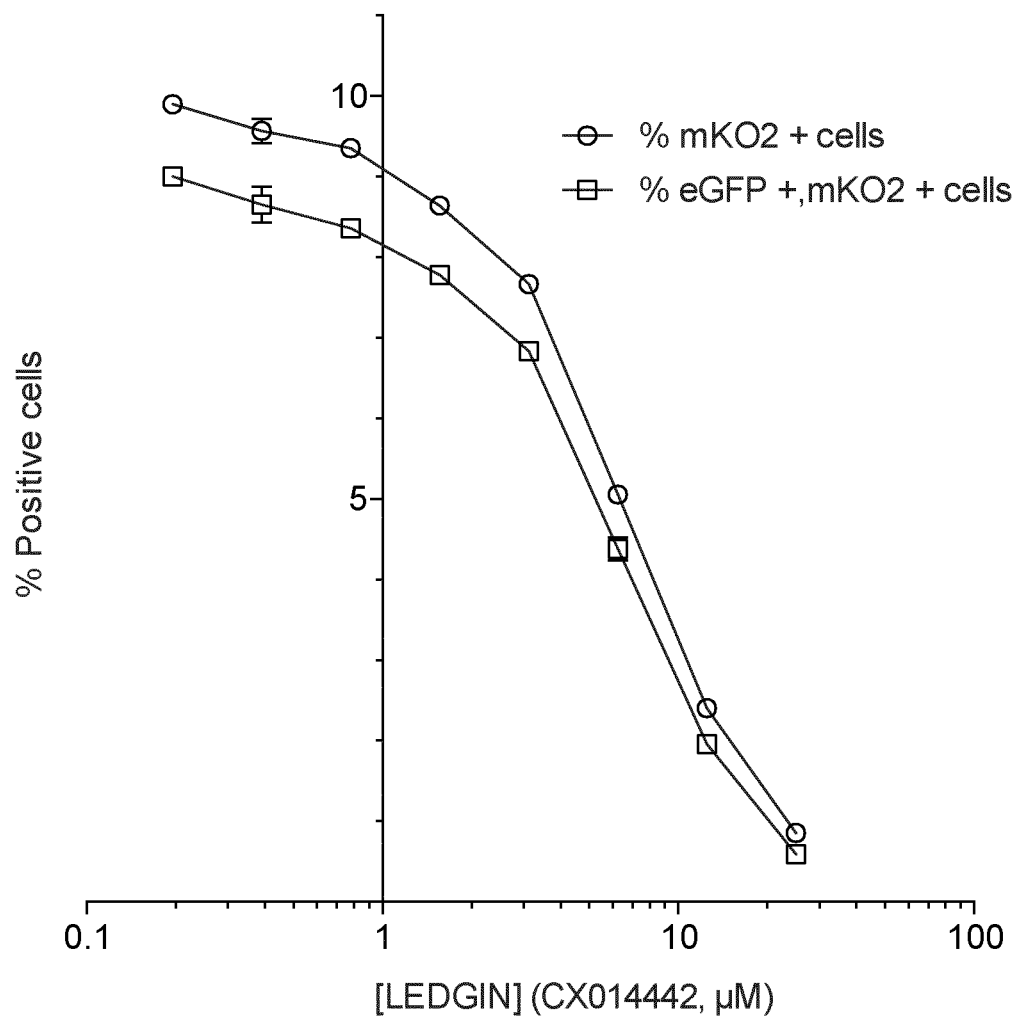
FIG. 7. LEDGIN treatment inhibits integration, induces quiescence of the residual viral reservoir and reduces reactivation in primary CD4+ T cells. (a) Activated CD4+ T-cells were infected with single round double reporter virus (OGH) and the % eGFP and % mKO2 positive cells were monitored. Dose-response curve shows a decrease both in the % eGFP+, mKO2+ cells and overall % mKO2+ cells with increasing LEDGIN (CX014442) concentration. (b) The fraction of silently infected cell population (% eGFP−, mKO2+ cells)/(% mKO2+ cells)*100 increased upon addition of LEDGINs. Data are representative for two different donors. All vectors were VSV-G pseudotyped. GFP, Enhanced Green Fluorescent Protein; mKO2, Mutant Kusubira Orange 2. (c) Activated CD4+ T-cells were infected with NL4.3 virus under different LEDGIN concentrations. 4 days p.i. integrated copy numbers were determined using a quantitative Alu-LTR PCR. (d) 4 days p.i. CD4+ T-cells were reactivated using PMA/PHA and p24 production in the supernatant was monitored 7 days p.i. by ELISA. The average data for two different donors tested±SEM are shown. PHA, phytohaemagglutinin; PMA, phorbol 12-myristate 13-acetate.
Figure 7:
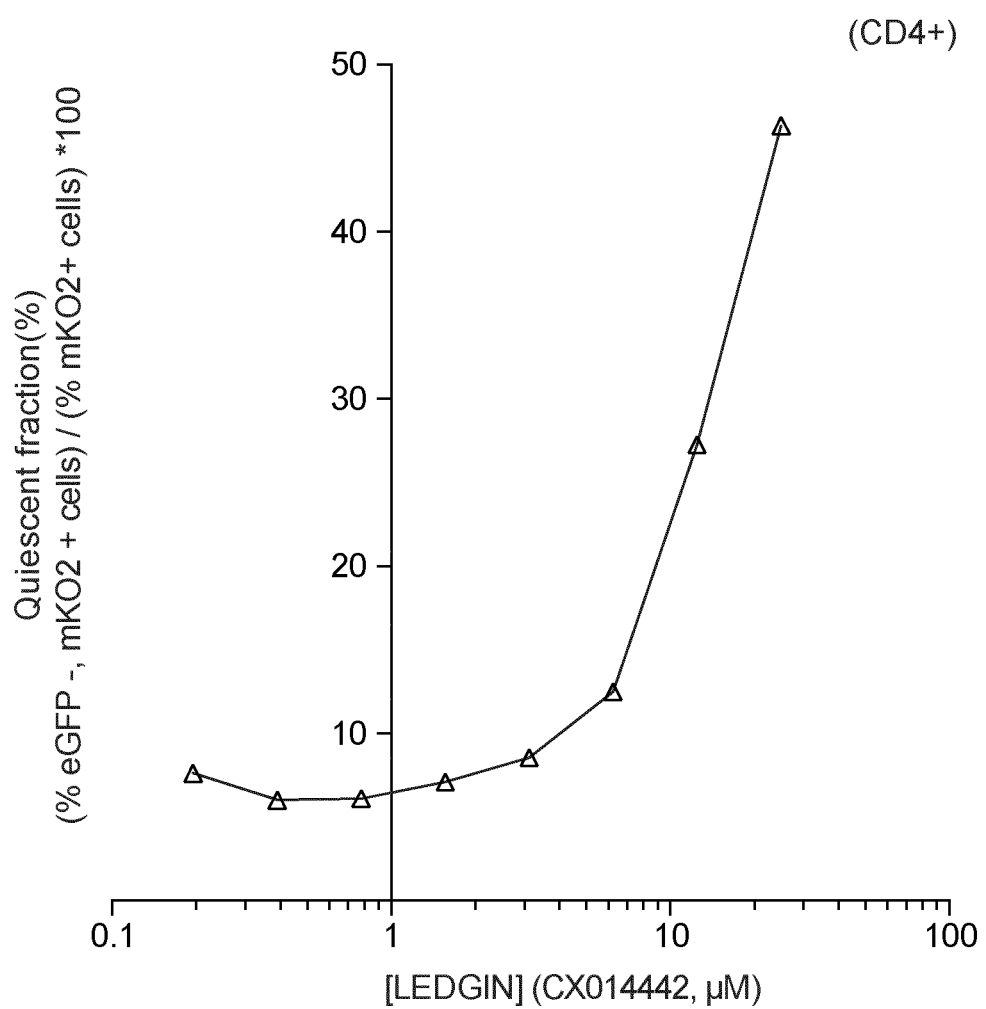
Figure 7:
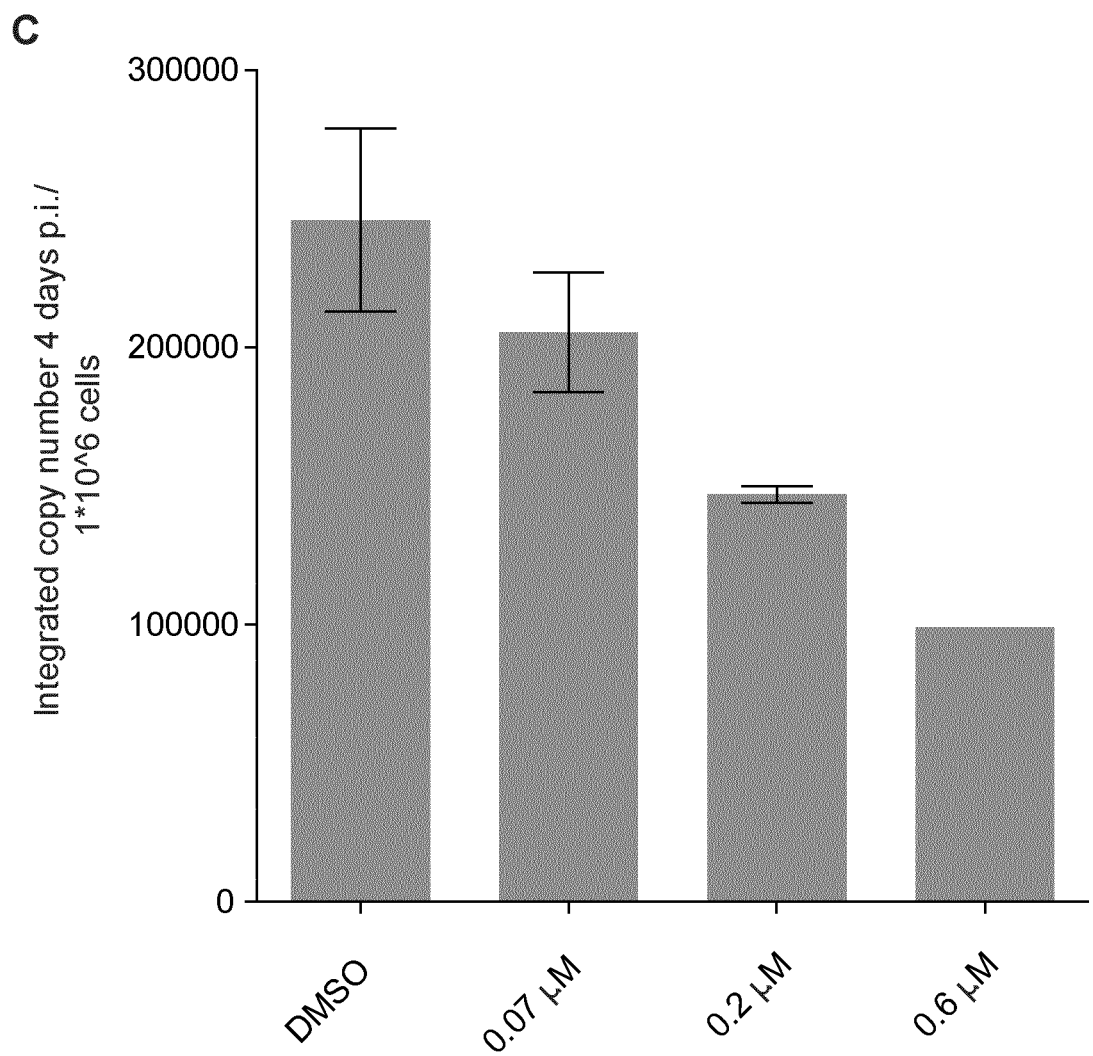
Figure 7:
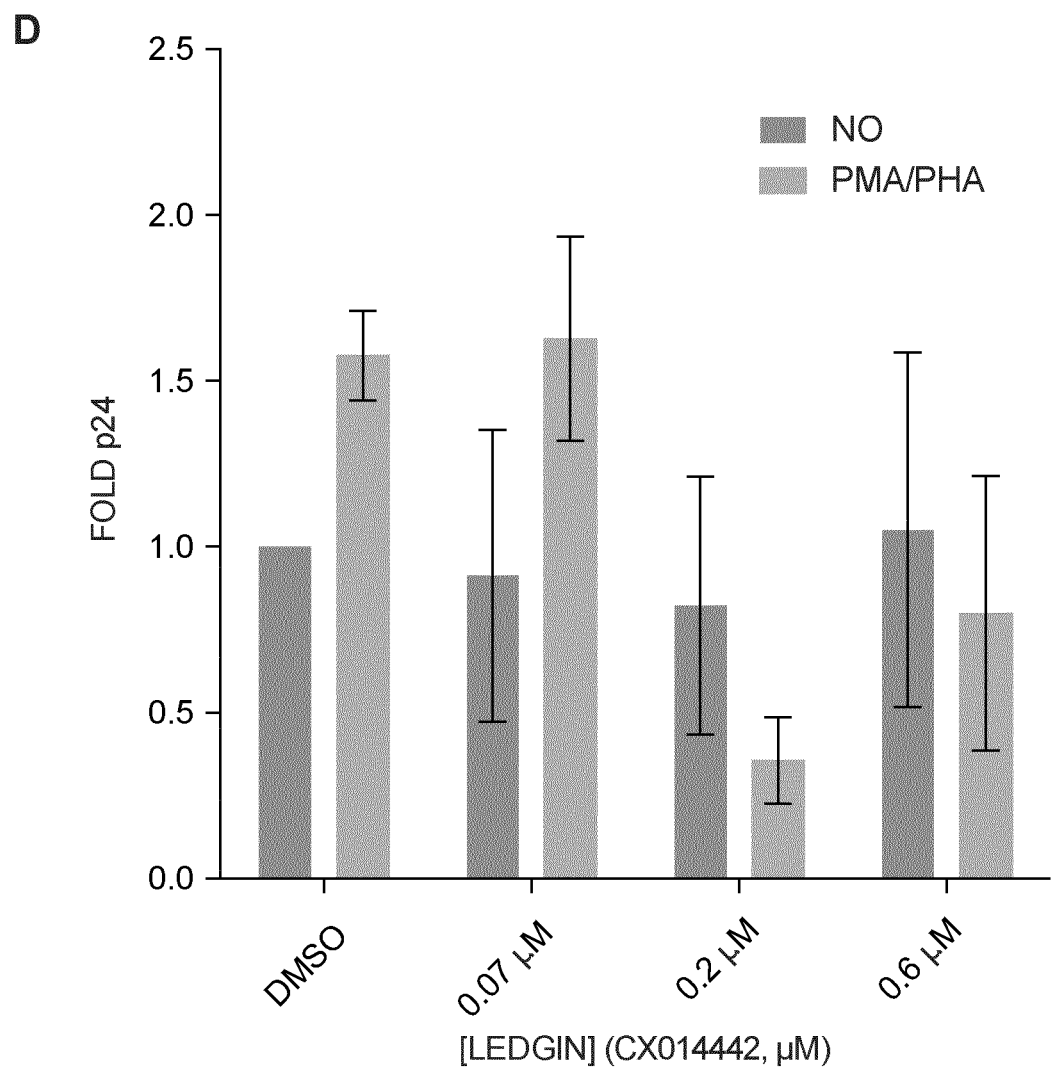

LEDGIN Treatment Inhibits Integration, Relatively Increases the Quiescent Viral Reservoir and Reduces Reactivation in Primary CD4+ T cells Since recent studies reported the existence of a latently infected cell population after infection of activated primary CD4+ T cells (Calvanese et al., 2013; Chavez et al., 2015; Dahabieh et al., 2013), we tried to corroborate the effect of LEDGIN treatment on proviral latency in this model. Human PBMCs were purified, selectively enriched for CD4+ T cells using Bi-specific MAb CD3.8 and infected with the OGH reporter virus, in the presence or absence of LEDGINs (FIG. 7a,b). Similar to the results observed in SupT1 cells, LEDGIN (CX014442) treatment induced a dose-dependent decrease in the % infected cells (decrease in % eGFP$^+$/mKO2$^+$ cells or overall % mKO 2$^+$ cells, FIG. 7a) and an increase in the fraction quiescent cells (% eGFP$^-$, mKO2$^+$ cells)/(% mKO2$^+$ cells)*100 (FIG. 7b) reaching 46.3% quiescence at a CX014442 concentration of 25 µM (representative data from one donor are shown for 2 different donors tested). Next we evaluated the multimodal effect of LEDGIN treatment on integration, assembly and reactivation in a multiple round reactivation model using WT HIV in resting CD4+ T-cells in order to model the in vivo situation. PHA/IL-2 activated primary (resting) CD4+ T cells were infected with NL4.3 virus in the presence of submicromolar concentrations of LEDGINs. At day four post infection (p.i.) LEDGINs were removed and cells were reseeded in the presence of PMA and PHA. Virus production upon reactivation was measured at day 7 p.i. by p24 ELISA. LEDGIN treatment reduced the number of proviral DNA copies in CD4+ T-cells in a dose-dependent manner (FIG. 7c). These residual integrants were less susceptible to reactivation as displayed by the reduced p24 production (FIG. 7d, data show the average for two different donors tested). Apart from reducing overall integration, these data suggested that LEDGIN treatment during HIV infection leads to quiescence of the residual integrants both in SupT1 and primary CD4+ T-cells. This quiescent reservoir appears less susceptible to reactivation.

Materials and Methods

Cell Culture, Virus Production and Transduction

All cells were cultured in a humidified atmosphere containing 5% CO2 at 37° C. SupT1 (provided by the National Institutes of Health Reagent Program, National Institutes of Health, Bethesda, Md.) and Nalm cells were cultured in Roswell Park Memorial Institutes medium (RPMI, GIBCO-BRL, Merelbeke, Belgium) supplemented with 10% v/v heat inactivated fetal calf serum FCS (Sigma-Aldrich, Bornem, Belgium) and 0.01% w/v gentamicin (GIBCO). HEK 293T cells (gift from O. Danos, Evry, France) were cultured in DMEM medium (GIBCO) with 5% v/v FCS (Sigma-Aldrich) and 0.01% w/v gentamicin (GIBCO). Vesicular stomatitis virus G (VSV-G) pseudotyped viruses were generated by double transfection of HEK293T cells with plasmid encoding a single round HIV clone (pNL4-3.tCD34.R-.E-, pOGH, pOGH-csGFP-only, pOGH-mkO2-only) together with a VSV-G encoding plasmid (pVSVG) using linear polyethylenimine (PEI; Polysciences, Amsterdam, The Netherlands). Medium was replaced 6 h post transfection and supernatant collected after 72 h by filtration through a 0.22 µm-pore membrane (Corning Inc., Seneffe, Belgium). The virus was concentrated using a Vivaspin 15 50 kDa cut-off column (Vivascience, Bornem, Belgium), DNase treated and stored at −80° C. Cells were seeded and infected for 3 days in 48-well plates yielding an infection rate <40% positive cells, as monitored by FACS analysis using a MACS Quant VYB FACS analyzer (Miltenyi Biotech GmbH), ensuring single-copy integrants. 72 hours post infection cells were washed twice in PBS to remove residual virus and reseeded. FACS samples were taken every 2 days to monitor reporter gene expression.

Reporter Viruses

*Multi-Colored Reporter Virus (OGH)

A variant of the recently described LAI-based double reporter virus was used where a constitutive and a LTR-driven reporter are simultaneously measured to study the latent reservoir (Calvanese et al., 2013; Dahabieh et al., 2013). This orange-green HIV-1 (OGH) reporter virus variant encodes LTR-driven enhanced Green Fluorescent Protein (eGFP) at the nef gene position and contains as well a constitutively active EF1alpha promoter driving mutant Kusabira-Orange2 (mKO2) expression instead of mCherry as described by (Calvanese et al., 2013) (FIG. 1a,b). An internal constitutive promoter driving mKO2 expression allows direct visualization of the LTR-silent latent proviral pool via the FACS measurement of mKO2-based red fluorescence.

*HIV NL4-3.tCD34.R-.E-

HIV tCD34 is a NL4.3-based single round reporter virus containing the LTR driven truncated tCD34 as a reporter protein in the nef gene position (FIG. 2a). We replaced the firefly luciferase gene in pNL4-3.Luc.R-.E- (NIH aids reagent program) via NotI-XhoI digestion with a tCD34 cassette using standard PCR amplification methods. CD34, or cluster of differentiation 34, is a cell surface glycoprotein functioning as a cell-cell adhesion factor in HSCs but is not present on primary CD4+ T lymphocytes (Fehse et al., 2000). A truncated version was used to block signal transduction and expression was visualized using antibody-staining allowing for non-fluorescent based cell sorting. Human CD34-PE antibody (Miltenyi Biotec, Cat.No 130-081-002) was used to detect tCD34 expression.

Flow Cytometry analysis

Prior to flow cytometry cells were fixed for 15 min in 4% Paraformaldehyde PAF at room temperature. Expression of eGFP/mKO2 or tCD34 was monitored using a MACS Quant VYB FACS analyzer (Miltenyi Biotech GmbH) using a 488 nm, 50 mW DPSS (diode pumped solide state) and 561 nm, 100 mW diode laser respectively and 525/50 nm-586/15 nm band pass filters. A total of at least 20,000 live cells were counted, as determined on the basis of forward scatter channel-side scatter channel (FSC-H/SSC-H) and doublets were excluded based on the FSC-A/FSC-H or SSC-A/SSC-H plot. Data were analyzed using a third party-software (FlowJo).

Drug Treatment

LEDGINs (CX014442) were added at different concentrations during single round infection where indicated and washed away together with residual virus 72 hours post infection. Samples were harvested for FACS analysis and the remainder of infected cells was reseeded. FACS samples were taken every 2 days to monitor reporter gene expression. 11 days post infection the infected cells were reactivated from latency using TNFalpha (10 ng/mL, Immunosource), SAHA (0.3 to 3 µM, AIDS reagents), prostratin (5 µM, AIDS reagents) or PMA (0.3 µM, AIDS reagents) 24 hours prior to analysis by flow cytometry. Time courses and drug concentrations are indicated in the individual experiments. LEDGINs were synthesized by the Cistim/CD3-facility (courtesy of Dr. A. Marchand).

gDNA Isolation and Quantifcation of Integrated Copy Number

Two million cells were pelleted and genomic DNA extracted using a mammalian genomic DNA miniprep kit (Sigma-Aldrich). Standard spectrophotometric methods were used to determine the genomic DNA concentration. Samples corresponding to 250 ng genomic DNA were used for analysis. Each reaction contained 12.5 µl iQ Supermix (Biorad, Nazareth, Belgium), 40 nmol/l forward and reverse primer (5' TGCACCCTGTGTCTCAACAT 3' (SEQ ID NO: 1) and 5' GGCTTCAAGGTTGTCTCTGG 3' (SEQ IS NO: 2) respectively) and 40 nmol/l of tCD34 probe (5' (6FAM)-ggccacaacaaacatcacag-(TAM) 3') (SEQ IS NO: 3) in a final volume of 25 µl. In all cases, RNaseP was used as an endogenous control for normalization (TaqMan RNaseP control reagent, Applied Biosystems, The Netherlands). Samples were run in triplicate for 3 minutes at 95° C. followed by 50 cycles of 10 seconds at 95° C. and 30 seconds at 55° C. in a LightCycler 480 (Roche-applied-science, Vilvoorde, Belgium). Analysis was performed using the LightCycler 480 software.

CD4+ T-cell Enrichment.

Human peripheral blood mononuclear cells (PBMCs), obtained from the Red Cross Blood transfusion Center (Mechelen, Belgium) according to approved bioethical guidelines of our institute (S57175-IRB00002047), were purified from fresh buffy coats using lymphoprep density gradient centrifugation (Stem cell technologies). The CD4+ T cells were selectively enriched using Bi-specific MAb CD3.8 (0.5 µg/mL, AIDS reagents) for 5 days. Cells were cultured in RPMI 1640, 15% v/v FBS, 0.1% v/v Gentamicin, 100 U/ml IL-2 (Peprotech) (T-cell medium, TCM). Enriched total CD4+ primary T cells were infected with single round reporter virus for 2 h at 37° C., washed twice in TCM and reseeded in medium containing different concentrations of LEDGIN CX014442. HIV infection was monitored 48 h post infection using flow cytometry analysis.

Reactivation of Latent Provirus in Primary CD4+ T-cells.

Peripheral blood mononuclear cells (PBMCs) were isolated from fresh buffy coats obtained from the Red Cross Blood transfusion center (Mechelen, Belgium) according to approved bioethical guidelines of our institute (557175-IRB00002047). Resting CD4+ T cells were purified using a custom-made EasySep negative selection kit (Stem Cell Technologies; 19052 cocktail, with the addition of CD25, CD69, and HLA-DR antibodies (catalogue number 19309VK)). The resulting 95% pure resting CD4+ T cells consisted of both naïve and central memory T cells (Sallusto et al., 1999). These freshly isolated resting CD4+ T cells were activated with 10 µg/ml PHA (Sigma-Aldrich) and 100 U/mL IL-2 (Peprotech) for 2 days before infecting with NL4.3 wt virus for 2 hrs ($3.5*10^3$ ng p24 per $1 \times 10^7$ cells/mL). Cells were washed twice with PBS and reseeded in the presence of varying concentrations of LEDGIN (CX014442) and 1 U/mL of IL-2. Four days post-infection cells were washed twice using PBS and some cells were harvested for quantification of integrated proviral DNA using real time PCR (nested Alu-LTR PCR, (Butler et al., 2001; Lewin et al., 2008) normalized for input DNA by qPCR for the CCR5 gene as previously described (Zhang et al., 1999). Other cells were reseeded in the presence of 10 nM PMA (Sigma-Aldrich) together with 10 µg/mL PHA (Sigma-Aldrich) or left untreated. PHA activated feeder peripheral blood mononuclear cells (PBMCs) were added 24 h after the activating stimulus to amplify virus replication and enhance detection of the infection (Saleh et al., 2011). Virus production was measured in culture supernatant at day 7 post-infection by p24 ELISA (Fujirebio Europe).

Statistical Analysis.

Reactivation results are expressed as means±standard error of the mean. Statistical analysis was assessed using multiple t tests and corrected using Sidak-Bonferroni with significance levels indicated. Ranked Wald statistics were used to calculate the statistical significance (asterisks) for a given genomic feature between integration site datasets relative to the DMSO treated condition (dashes). Significant deviation from the DMSO treated control dataset for safe harbor criteria was calculated using a Pearsons Chi-square test. ImageJ software was used to measure the relative distance of γH2AX foci to the nuclear rim. Statistical differences were calculated using a Kolmogorov-Smirnov test as described previously (Di Primio et al., 2013).

Virus Production in the Presence of LEDGINs

Vesicular stomatitis virus G (VSV-G)-pseudotyped single-round virus particles were generated by double transfection of HEK293T cells with a plasmid encoding a single-round HIV clone (pOGH) together with a VSV-G protein encoding plasmid (pVSVG). Linear polyethyleneimine (PEI; Polysciences) was used for plasmid transfections. Cells were washed 6 hrs post transfection (3× with PBS) and medium was added supplemented with a dilution series of LEDGIN CX014442 (0.27 µM–0.00375 µM). Supernatant was collected after 48 hrs by filtration through a 0.45 µm pore membrane (Corning Inc.). The virus was concentrated using a Vivaspin 15-50 kDa cut-off column (Vivascience), washed 3 times thoroughly with PBS in order to remove residual compound, DNase (Roche) treated and stored at −80° C. Virus productions from at least 10 petri dishes were used for each condition to reduce variation in production efficiency. Productions were normalized for p24/RT. SupT1 and THP1 cells were seeded and infected with equal RT units for 2 hours, washed twice and seeded in 48-well plates (10% FCS, 0.01% gentamicin RPMI). Cells were harvested 48 hours post infection yielding an infection rate <40% positive cells, as monitored by FACS analysis using a MACS Quant VYB FACS analyzer (Miltenyi Biotech GmbH), ensuring single-copy integration.

Measurement of Viral Reservoirs.

Measurement of viral reservoirs can be performed as described by Eriksson et al. 2013 (Pathology; February; 9 (2):e1003174) which is summarized below.

Digital Droplet PCR for Total HIV-1 DNA.

Cellular DNA is extracted using a Qiagen DNA Blood Midi Kit, following the manufacturer's protocol. DNA is ethanol precipitated following elution to increase concentration. The DNA concentration is estimated from the A260/A280 absorptivity ratio using a spectrophotometer. When the DNA concentration is below the desired concentration for emulsification, the concentration is increased by ethanol precipitation and re-suspension. Where specified, templates are thoroughly mixed with background human genomic DNA obtained by identical extraction methods from HIV-1 seronegative donors ("PBMC DNA") or with sonicated salmon sperm DNA. Extracted DNA is heated to 95° C. for 10 minutes, then quenched on ice prior to digestion with the restriction enzyme BSAJ-I (New England Biolabs) at 60° C. for 1 hour. Plasmids encoding the entire HIV-1 genome (pNL4-3, AIDS Reference Research Reagent Repository) can be used as standards. Primers to conserved regions of HIV-1 pol and to the HIV-1 LTR are used. An RPP30 (RNAse P) primer/probe set is used for host genomic DNA quantification. Samples are diluted 10-fold and RPP30 is assayed without multiplexing. The PCR reaction mixture is loaded into an emulsification device, and droplets are formed. The contents are transferred to a 96-well reaction plate and sealed with a pre-heated Eppendorf 96-well heat sealer for 2 seconds. Total DNA is amplified separately in a thermal cycler. Each reaction consists of a 20 µL solution containing 10 µL ddPCR Probe Supermix, 900 nM primers, 250 nM probe, and template DNA with the following cycling conditions: 10 minutes at 95° C., 40 cycles each consisting of a 30 second denaturation at 94° C. followed by a 58° C. extension for 60 seconds, and a final 10 minutes at 98° C. After cycling, droplets are analyzed immediately or stored at 4° C. overnight and until analysis.

Total cellular DNA input is measured by halving the estimated number of RPP30 copies, and copy numbers per diploid cell equivalent were computed as the ratio of template (pol or 2-LTR) copies per diploid cell.

Measurements of Integrated HIV-1 in Resting CD4$^+$T Cells and PBMC.

Integrated HIV-1 DNA is measured in PBMC or purified resting CD4$^+$ T cells using a previously described Alu PCR. This assay detects only integrated proviruses because it relies on an initial amplification in which one primer hybridizes with a conserved sequence in Alu elements which are present in ~2,000,000 copies in the human genome. The Alu primer is paired with an HIV-1 gag primer in the first round of amplification. This Alu-gag amplification is then followed by a second amplification that targets a sequence in the HIV-1 LTR (R-U5). The level of HIV-1 integration is quantitated by comparing the detection signal to an integration standard curve that correlates cycle thresholds with integration standard copy number. The integration standard can be especially produced to contain genomes with integration sites at a variety of distances from Alu sites, mimicking the pattern of integration seen in natural infection. DNA is isolated from frozen PBMC and resting CD4$^+$T cell pellets using a commercial kit. DNA is then diluted to 2 ug/mL and assayed in replicates for integrated HIV-1 proviruses. The first step reaction is performed for 40 cycles at the following conditions: 95° C. for 15 s, 50° C. for 15 s and 72° C. for 3 min 30 s. Simultaneously and on the same plate, the same number of reactions with only the gag primer are also performed following the same conditions. The product from the first step reaction is then diluted 1:2 into the $2^{nd}$ step master mix. The second step is performed for 50 cycles. The cycle threshold values are then used to calculate an integration value using a standard curve. In samples with low levels of integrated HIV-1 DNA (with integration detectable in <30% of wells), the percent positive method for calculation can be utilized. In these cases, a cutoff value can be generated by subtracting two standard deviations from the average of the cycle threshold values for PCR reactions with only the gag primer present in the first step. Any wells with a cycle threshold less than this cutoff value can be considered "positive" signals. The percent of positive signals is calculated by dividing the wells counted by the total number of wells assayed (containing both the Alu and gag primers). A standard curve showing a linear relationship between the copies of integrated HIV-1 and the percent of positive wells is used to calculate copy number in several of these samples.

LEDGF/p75-HIV-1 Integrase Interaction Screening: Alphascreen Assay

Alphascreen (Amplified Luminescent Proximity Homogeneous Assay) is a bead-based technology used to study biomolecular interactions in a microtiterplate format. Binding of integrase and LEDGF/p75 leads to an energy transfer from the donor to the acceptor bead. This transfer induces the emission of luminescence/fluorescence. Inhibition of the interaction decreases the emission in a concentration dependent manner.

The AlphaScreen assay is performed according to the manufacturer's protocol (Perkin Elmer, Benelux). Reactions are performed in 25 µl final volume in 384-well Optiwell™ microtiter plates (Perkin Elmer). The reaction buffer contains 25 mM Tris-HCl (pH 7.4), 150 mM NaCl, 1 mM MgCl$_2$, 0.01% (v/v) Tween-20 and 0.1% (w/v) bovine serum albumin. His$_6$-tagged integrase (300 nM final concentration) is incubated with the compounds for 30 min at 4° C. The compounds are added in varying concentrations normally spanning a wide range from 0.1 up to 100 µM. Afterwards 100 nM flag-LEDGF/p75 is added and incubation is prolonged for an additional hour at 4° C. Subsequently 5 µl of Ni-chelate-coated acceptor beads and 5µl anti-flag donor beads are added to a final concentration of 20 µg/ml of both beads. Proteins and beads are incubated for 1 h at 30° C. in order to allow association to occur. Exposure of the reaction to direct light is omitted as much as possible and the emission of light from the acceptor beads is measured in the EnVision plate reader (Perkin Elmer, Benelux) and analyzed using the EnVision manager software.

REFERENCES

Butler, S. L., Hansen, M. S., and Bushman, F. D. (2001). A quantitative assay for HIV DNA integration in vivo. Nature Medicine 7, 631-634.

Calvanese, V., Chavez, L., Laurent, T., Ding, S., and Verdin, E. (2013). Dual-color HIV reporters trace a population of latently infected cells and enable their purification. Virology 446, 283-292.

Cherepanov, P., Maertens, G., Proost, P., Devreese, B., Van Beeumen, J., Engelborghs, Y., De Clercq, E., and Debyser, Z. (2003). HIV-1 integrase forms stable tetramers and associates with LEDGF/p75 protein in human cells. Journal of Biological Chemistry 278, 372-381.

Christ, F., and Debyser, Z. (2013). The LEDGF/p75 integrase interaction, a novel target for anti-HIV therapy. Virology 435, 102-109.

Christ, F., Voet, A., Marchand, A., Nicolet, S., Desimmie, B. A., Marchand, D., Bardiot, D., Van der Veken, N. J., Van Remoortel, B., Strelkov, S. V., et al. (2010). Rational design of small-molecule inhibitors of the LEDGF/p75-integrase interaction and HIV replication. Nature Chemical Biology 6, 442-448.

Dahabieh, M. S., Ooms, M., Simon, V., and Sadowski, I. (2013). A doubly fluorescent HIV-1 reporter shows that the majority of integrated HIV-1 is latent shortly after infection. Journal of Virology 87, 4716-4727.

De Ravin, S. S., Su, L., Theobald, N., Choi, U., Macpherson, J. L., Poidinger, M., Symonds, G., Pond, S. M., Ferris, A. L., Hughes, S. H., et al. (2014). Enhancers are major targets for murine leukemia virus vector integration. Journal of Virology 88, 4504-4513.

Debyser, Z., Christ, F., De Rijck, J., and Gijsbers, R. (2015). Host factors for retroviral integration site selection. Trends Biochem. Sci. 40, 108-116.

Demeulemeester, J., Chaltin, P., Marchand, A., De Maeyer, M., Debyser, Z., and Christ, F. (2014). LEDGINs, non-catalytic site inhibitors of HIV-1 integrase: a patent review (2006-2014). Expert Opin Ther Pat 24, 609-632.

Di Primio, C., Quercioli, V., Allouch, A., Gijsbers, R., Christ, F., Debyser, Z., Arosio, D., and Cereseto, A. (2013). Single-cell imaging of HIV-1 provirus (SCIP). Proc. Natl. Acad. Sci. U.S.a. 110, 5636-5641.

Fehse, B., Richters, A., Putimtseva-Scharf, K., Klump, H., Li, Z., Ostertag, W., Zander, A. R., and Baum, C. (2000). CD34 splice variant: an attractive marker for selection of gene-modified cells. Molecular Therapy 1, 448-456.

Gijsbers, R., Ronen, K., Vets, S., Malani, N., De Rijck, J., McNeely, M., Bushman, F. D., and Debyser, Z. (2009). LEDGF Hybrids Efficiently Retarget Lentiviral Integration Into Heterochromatin. Molecular Therapy 18, 552-560.

Jurado, K. A., Wang, H., Slaughter, A., Feng, L., Kessl, J. J., Koh, Y., Wang, W., Ballandras-Colas, A., Patel, P. A., Fuchs, J. R., et al. (2013). Allosteric integrase inhibitor potency is determined through the inhibition of HIV-1 particle maturation. Proc. Natl. Acad. Sci. U.S.a. 110, 8690-8695.

Lewin, S. R., Murray, J. M., Solomon, A., Wightman, F., Cameron, P. U., Purcell, D. J., Zaunders, J. J., Grey, P., Bloch, M., Smith, D., et al. (2008). Virologic determinants of success after structured treatment interruptions of antiretrovirals in acute HIV-1 infection. J. Acquir. Immune Defic. Syndr. 47, 140-147.

Marshall, H. M., Ronen, K., Berry, C., Llano, M., Sutherland, H., Saenz, D., Bickmore, W., Poeschla, E., and Bushman, F. D. (2007). Role of PSIP1/LEDGF/p75 in Lentiviral Infectivity and Integration Targeting. PLoS ONE 2, e1340.

Papapetrou, E. P., Lee, G., Malani, N., Setty, M., Riviere, I., Tirunagari, L. M. S., Kadota, K., Roth, S. L., Giardina, P., Viale, A., et al. (2011). Genomic safe harbors permit high β-globin transgene expression in thalassemia induced pluripotent stem cells. Nat Biotechnol 29, 73-78.

Pauwels, R., Balzarini, J., Baba, M., Snoeck, R., Schols, D., Herdewijn, P., Desmyter, J., and De Clercq, E. (1988). Rapid and automated tetrazolium-based colorimetric assay for the detection of anti-HIV compounds. Journal of Virological Methods 20, 309-321.

Saleh, S., Wightman, F., Ramanayake, S., Alexander, M., Kumar, N., Khoury, G., Pereira, C., Purcell, D., Cameron, P. U., and Lewin, S. R. (2011). Expression and reactivation of HIV in a chemokine induced model of HIV latency in primary resting CD4+ T cells. Retrovirology 8, 80.

Sallusto, F., Lenig, D., Förster, R., Lipp, M., and Lanzavecchia, A. (1999). Two subsets of memory T lymphocytes with distinct homing potentials and effector functions. Nature 401, 708-712.

Schrijvers, R., De Rijck, J., Demeulemeester, J., Adachi, N., Vets, S., Ronen, K., Christ, F., Bushman, F. D., Debyser, Z., and Gijsbers, R. (2012). LEDGF/p75-Independent HIV-1 Replication Demonstrates a Role for HRP-2 and Remains Sensitive to Inhibition by LEDGINs. PLoS Pathog 8, e1002558.

Zhang, Z., Schuler, T., Zupancic, M., Wietgrefe, S., Staskus, K. A., Reimann, K. A., Reinhart, T. A., Rogan, M., Cavert, W., Miller, C. J., et al. (1999). Sexual transmission and propagation of SIV and HIV in resting and activated CD4+ T cells. Science 286, 1353-1357.

Powell, S K, Rivera-Soto, R, Gray S (2015). Viral Expression Cassette Elements to Enhance Transgene Target Specificity and Expression in Gene Therapy Discov Med. 102:49-57

---

The invention claimed is:

1. A method of treating a retroviral infection in a subject by suppressing the reactivation potential of the retroviral reservoir, which method comprises
    (a) administering to the subject during active replication and integration of the virus a compound which binds to the lens epithelium-derived growth factor (LEDGF/p75) binding pocket of human immune deficiency (HIV)-integrase (IN) and prevents binding of IN to LEDGF/p75 to direct retroviral integration into transcriptionally silent positions in the genome of T cells; and
    (b) determining the reactivation potential of the retroviral reservoir of T cells in said subject by a viral outgrowth assay, wherein said administration of said compound is maintained until said reactivation potential is determined as non-existent in said assay, and said retroviral infection is effectively treated by providing a remission of the retroviral infection, wherein said compound is a 2-(quinolin-3-yl) acetic acid derivative.

2. The method according to claim 1, wherein said compound is administered at a daily dosage that is equal to or higher than the dosage envisaged for use in standard therapy.

3. The method of claim 1, wherein said compound is administered at a daily dosage that is a dosage which ensures a trough concentration in the blood which is at least times 5 times the antiviral EC50 of said compound.

4. The method according to claim 1, wherein said subject has received standard anti-retroviral combination therapy and said antiretroviral combination therapy is interrupted prior to said administration of said compound.

5. The method according to claim 1, wherein said subject is a treatment-naive subject.

6. The method according to claim 1, wherein said compound is administered as part of an anti-retroviral combination therapy.

7. The method according to claim 1, wherein said compound is administered daily during a discrete period of 1 to 24 weeks, and the reactivation potential of the retroviral reservoir is determined after said discrete period of 1 to 24 weeks.

8. The method according to claim 1, wherein said method comprises administering said drug as a monotherapy.

9. The method according to claim 1, wherein said 2-(quinolin-3-yl) acetic acid derivative is 2-(6-chloro-2-methyl-4-phenylquinolin-3-yl) pentanoic acid.

* * * * *